US011986660B2

(12) United States Patent
Schouenborg et al.

(10) Patent No.: US 11,986,660 B2
(45) Date of Patent: *May 21, 2024

(54) METHOD AND SYSTEM FOR IMPROVING STIMULATION OF EXCITABLE TISSUE

(71) Applicant: NEURONANO AB, Karlshamn (SE)

(72) Inventors: Jens Schouenborg, Lund (SE); Hjalmar Bjartmarz, Höllviken (SE)

(73) Assignee: NEURONANO AB, Karlshamn (SE)

(*) Notice: Subject to any disclaimer, the term of this patent is extended or adjusted under 35 U.S.C. 154(b) by 0 days.

This patent is subject to a terminal disclaimer.

(21) Appl. No.: 17/549,065

(22) Filed: Dec. 13, 2021

(65) Prior Publication Data

US 2022/0096838 A1    Mar. 31, 2022

Related U.S. Application Data

(63) Continuation of application No. 15/737,236, filed as application No. PCT/SE2016/050698 on Jul. 7, 2016, now Pat. No. 11,198,003.

(30) Foreign Application Priority Data

Jul. 10, 2015  (SE) .................................. 1551013-4
Jun. 3, 2016  (WO) ................. PCT/SE2016/050534

(51) Int. Cl.
*A61N 1/36* (2006.01)
*A61B 5/24* (2021.01)
(Continued)

(52) U.S. Cl.
CPC ............ *A61N 1/36132* (2013.01); *A61B 5/24* (2021.01); *A61B 5/377* (2021.01); *A61N 1/0534* (2013.01);
(Continued)

(58) Field of Classification Search
CPC ............ A61B 5/377; A61B 2562/0209; A61B 2562/046; A61N 1/0534; A61N 1/36139; A61N 1/36185; A61N 1/378
See application file for complete search history.

(56) References Cited

U.S. PATENT DOCUMENTS 6,427,086 B1  7/2002  Fischell et al.
7,305,268 B2  12/2007  Gliner et al.
(Continued)

FOREIGN PATENT DOCUMENTS

EP          2529789 A1     12/2012
WO      2007040442 A1      4/2007
(Continued)

OTHER PUBLICATIONS

Lind et al., "Gelatine-embedded electrodes—a novel biocompatible vehicle allowing implantation of highly flexible microelectrodes", Journal of Neural Engineering 2010 7, 046005, p. 1-14, Jun. 16, 2010.
(Continued)

*Primary Examiner* — Mallika D Fairchild
(74) *Attorney, Agent, or Firm* — Capitol City TechLaw

(57) ABSTRACT

A method is provided for optimization of a stimulation specificity and an energy consumption of implanted electrodes in excitable tissue of a patient. The method may involve electrically stimulating excitable tissue between one or more combinations of electrode pairs in a cluster of electrodes, or electrically stimulating excitable tissue between one or more combinations of electrode pairs in two or more clusters of electrodes. The two electrodes of the electrode pairs may not belong to a same cluster. Each of the electrodes may be located on a physically separated entity, such that the tissue surrounds and separates each electrode from all other electrodes, thereby allowing tissue between the electrodes to be stimulated. An electrode pair or pairs
(Continued)

which give rise to a lowest energy consumption while still giving a therapeutic effect may be chosen. Alternatively, each electrode pair may be assigned a value related to the information provided by the patient and the energy consumption, and the electrode pair or pairs which give(s) rise to a most favorable assigned value may be chosen.

37 Claims, 1 Drawing Sheet

(51) Int. Cl.
  A61B 5/377 (2021.01)
  A61N 1/05 (2006.01)
  A61N 1/372 (2006.01)
  A61N 1/378 (2006.01)

(52) U.S. Cl.
  CPC ..... A61N 1/36064 (2013.01); A61N 1/36067 (2013.01); A61N 1/36071 (2013.01); A61N 1/36085 (2013.01); A61N 1/36096 (2013.01); A61N 1/36139 (2013.01); A61N 1/36175 (2013.01); A61N 1/36185 (2013.01); A61N 1/37241 (2013.01); A61N 1/37247 (2013.01); A61N 1/378 (2013.01); A61B 2562/0209 (2013.01); A61B 2562/046 (2013.01); A61N 1/05 (2013.01); A61N 1/36114 (2013.01)

(56) References Cited

U.S. PATENT DOCUMENTS

| | | | |
|---|---|---|---|
| 7,596,410 | B1 | 9/2009 | Kroll et al. |
| 9,138,585 | B2 | 9/2015 | Saha et al. |
| 9,433,779 | B2 | 9/2016 | Shelton et al. |
| 2001/0014820 | A1 | 8/2001 | Gielen et al. |
| 2002/0062143 | A1* | 5/2002 | Baudino ............ A61N 1/36071 607/116 |
| 2002/0116042 | A1 | 8/2002 | Boling |
| 2004/0034394 | A1 | 2/2004 | Woods et al. |
| 2004/0215288 | A1 | 10/2004 | Lee et al. |
| 2005/0060009 | A1 | 3/2005 | Goetz |
| 2005/0075681 | A1 | 4/2005 | Rezai et al. |
| 2006/0195159 | A1 | 8/2006 | Bradley et al. |
| 2006/0206163 | A1 | 9/2006 | Wahlstrand et al. |
| 2006/0265039 | A1 | 11/2006 | Bartic et al. |
| 2007/0203545 | A1 | 8/2007 | Stone et al. |
| 2008/0215119 | A1 | 9/2008 | Woods et al. |
| 2008/0255634 | A1 | 10/2008 | Jaax et al. |
| 2009/0088816 | A1 | 4/2009 | Harel et al. |
| 2010/0137943 | A1 | 6/2010 | Zhu |
| 2011/0093045 | A1 | 4/2011 | Moffitt |
| 2011/0144521 | A1 | 6/2011 | Molnar et al. |
| 2011/0144715 | A1 | 6/2011 | Molnar et al. |
| 2011/0230933 | A1 | 9/2011 | Choi et al. |
| 2011/0264165 | A1 | 10/2011 | Molnar et al. |
| 2011/0264171 | A1 | 10/2011 | Torgerson |
| 2012/0035685 | A1 | 2/2012 | Saha et al. |
| 2012/0053449 | A1 | 3/2012 | Moses et al. |
| 2012/0053649 | A1* | 3/2012 | Liu ............ A61N 1/0529 607/9 |
| 2012/0065699 | A1 | 3/2012 | Bedenbaugh |
| 2012/0238831 | A1 | 9/2012 | Benford |
| 2012/0271382 | A1 | 10/2012 | Arcot-Krishnamurthy et al. |
| 2012/0277621 | A1 | 11/2012 | Gerber et al. |
| 2012/0290042 | A1 | 11/2012 | Imran et al. |
| 2012/0302912 | A1 | 11/2012 | Moffitt et al. |
| 2012/0310305 | A1 | 12/2012 | Kaula et al. |
| 2012/0316619 | A1 | 12/2012 | Goetz et al. |
| 2013/0060302 | A1 | 3/2013 | Polefko et al. |
| 2013/0085361 | A1 | 4/2013 | Mercanzini et al. |
| 2013/0085537 | A1 | 4/2013 | Mashiach |
| 2013/0102857 | A1 | 4/2013 | Wolfberg et al. |
| 2013/0289667 | A1 | 10/2013 | Wacnik et al. |
| 2013/0296972 | A1 | 11/2013 | Polefko et al. |
| 2014/0066949 | A1 | 3/2014 | Eskuri |
| 2014/0249599 | A1 | 9/2014 | Kaula et al. |
| 2014/0277261 | A1 | 9/2014 | Rao et al. |
| 2014/0288620 | A1 | 9/2014 | DiLorenzo |
| 2014/0324117 | A1 | 10/2014 | Bodenbaugh |
| 2015/0126802 | A1 | 5/2015 | Lim et al. |
| 2015/0173636 | A1 | 6/2015 | Mokelke et al. |
| 2015/0202447 | A1 | 7/2015 | Afshar et al. |
| 2016/0199651 | A1 | 7/2016 | Meadows et al. |
| 2017/0105641 | A1 | 4/2017 | Boers et al. |

FOREIGN PATENT DOCUMENTS

| | | |
|---|---|---|
| WO | 2008005142 A1 | 1/2008 |
| WO | 2008091197 A1 | 7/2008 |
| WO | 2009075625 A1 | 6/2009 |
| WO | 2009158495 A1 | 12/2009 |
| WO | 2010144016 A1 | 12/2010 |
| WO | 2012025596 A2 | 3/2012 |
| WO | 2013191612 A1 | 12/2013 |

OTHER PUBLICATIONS

Thelin et al., "Implant Size and Fixation Mode Strongly Influence Tissue Reactions in the CNS", PLoS ONE, vol. 6 (Issue 1), e16267, p. 1-10, Jan. 26, 2011.

Kandel et al., "Principles of Neural Science", fourth edition, McGraw-Hill Companies, Inc., New York, p. 1-1230, 2000.

* cited by examiner

METHOD AND SYSTEM FOR IMPROVING STIMULATION OF EXCITABLE TISSUE

This application is a continuation application of U.S. patent application Ser. No. 15/737,236 filed Dec. 15, 2017, which is a US National Phase Application of International Application No. PCT/SE2016/050698 filed Jul. 7, 2016, the entire contents of both of which are incorporated herein by reference.

This application claims priority under 35 USC § 119(a)-(d) to SE patent application No. 1551013-4 filed Jul. 10, 2015, and PCT patent application No. PCT/SE2016/050534 filed Jun. 3, 2016, the entire contents of both of which are incorporated herein by reference.

TECHNICAL FIELD

The present invention refers to a method for optimization of the stimulation pattern of implanted electrodes in excitable tissue of a patient and to a system for performing said optimization.

BACKGROUND ART

Deep Brain Stimulation (DBS) was introduced for the treatment of neurological diseases such as Parkinson's disease in the eighties. The technique stimulates nervous tissue using an electrode device (alternatively called probe) that is implanted into deep nuclei of the brain. The mechanisms underlying the therapeutic effects are only partly understood but are thought to involve inhibition of abnormal neural activity. The DBS probe design used in the clinic has remained largely unchanged although more channels have been added to present versions. However, these probes still exhibit substantial limitations in stimulation specificity and biocompatibility. Consequently, such probes are prone to produce side effects and loss of therapeutic efficiency over time. At least three features of the design underlie these shortcomings: 1) detailed control of the distribution of current in the target tissue is prevented by the large size of the active electrode surfaces of the DBS electrodes combined with a distribution of these electrodes along the same probe, 2) it is difficult to predict the optimal stimulation sites in a given patient as the neural mechanisms underlying the beneficial effects of DBS are not fully understood and are due to individual variation in functional anatomy, 3) current electrode designs produce substantial glial scarring, that displaces neurons away from the active electrode sites. In turn, the glial scarring necessitates higher current intensities to achieve neural stimulation and results in a larger stimulation spread. A further problem is the shortening of battery life due to high current intensities resulting in repeated recharging or surgical replacement of the battery.

The state of art of devices for implantation into soft tissue also comprises microelectrodes. Microelectrodes have a wide field of application in medicine and related fields. In principle, electric signals emanating from single nerve cells or group of cells can be recorded. Single nerve cells or group of cells can also be electrically stimulated by such devices, and their reaction to such stimulation can be monitored. Several types of multichannel microelectrodes are known in the art (see e.g. WO 2007/040442, WO 2008/091197, WO 2009/075625, WO 2010/144016, WO 2012/025596 and WO 2013/191612).

US 2006/0195159 discloses a method of selecting a subset of electrodes in a stimulator device implanted in a patient in order to obtain an optimal therapeutic patient outcome.

US 2012/0302912 discloses a method for stimulation treatment wherein electrical stimulation is given via an electrode array in accordance with a set of stimulation parameters relating to both electrode combinations and electrical pulse parameters.

Multichannel electrodes offer the possibility of providing a precise stimulation pattern. Given that the functional anatomy of the brain is not identical for different patients due to e.g. congenital variations, structural changes caused by aging and degenerative diseases, and to experience dependent alterations in neuronal networks, the precise stimulation pattern causing a beneficial effect with minimal side effects needs to be evaluated in each patient. It is known to relate the implanted electrodes to known anatomical landmarks using imaging techniques such as computer tomography (CT) and magnetic resonance imaging (MRI) and observing the effects in the patient caused by the stimulation through the implanted electrodes. However, in many instances beneficial effects and side effects of a given stimulation pattern may take considerable time to establish. Hence, the time consumption to optimize the stimulation pattern becomes problematic when using multichannel electrode devices comprising a large number of electrodes.

Furthermore, it is also desirable to define a therapeutically useful stimulation pattern while keeping the energy consumption of the stimulation as low as possible, since this will reduce the risk of stimulation produced injury to the tissue and enhance the battery life time of the stimulating device connected to the implanted electrodes.

The objects of the present invention are to solve at least some of these problems and thereby improve the stimulation of excitable tissue, such as neuronal tissue or endocrine tissue of a patient with a view to curing or alleviating different diseases and disorders, including both physiological and psychological conditions. Additional objects will become obvious from the detailed description of the invention.

SUMMARY

An object with the present invention is to eliminate at least some of the above-mentioned problems and to provide a method and a system for optimization of the stimulation pattern of a set of implanted electrodes in excitable tissue of a patient, the patient being an animal or a human.

According to the invention, this object is achieved by means of a method and a system of the type mentioned by way of introduction, which have the features presented in the independent method claim and system claim, respectively. Different embodiments of said method and system are presented in the dependent claims, respectively.

More precisely, in a first aspect the present invention refers to a method for optimization of the stimulation pattern of a set of implanted electrodes in excitable tissue of a patient, wherein it comprises the steps of choosing a first group of a certain number of electrodes from said set of implanted electrodes, stimulating the excitable tissue electrically by said first group of electrodes, registering information provided by the patient, assigning each electrode of said first group of electrodes a value related to said information, and wherein the method is repeated for one or more further groups of said certain number of electrodes chosen from said set of implanted electrodes, wherein each electrode may be included in one or several groups, wherein the total assigned value for each electrode is calculated, and wherein electrodes having a total assigned value exceeding a predetermined value are chosen to be included in said stimulation pattern.

In a second aspect the present invention refers to the method according to said first aspect, wherein it also comprises steps for the reduction of the energy consumption.

In a third aspect the present invention refers to a method for treatment or alleviation of a disease or condition by use of a set of electrodes whose stimulation pattern has been optimized with the method according to claim 1, wherein the disease or condition is chosen from the group consisting of brain and/or spinal damage, lost functions, pain, Parkinson's disease, tremor, motor disorders, choreatic and other involuntary movements, memory disorders, Alzheimer's disease, degenerative diseases, epilepsy, mood disorders, aggression, anxiety, phobia, affect, sexual over-activity, impotence, eating disorders, sleep disorders, such as narcolepsy, attention disorders, stroke, damage of the brain, damage of the spinal cord, bladder disorders after spinal cord injury, bowel disorders after spinal cord injury, spasticity, somatosensory disorders, auditory disorders, visual disorders, and olfactory disorders.

In a fourth aspect the present invention refers to a system for optimization of the stimulation pattern of a set of implanted electrodes in excitable tissue of a patient and for treatment or alleviation of a disease or disorder with the method according to the present invention is also provided. The system comprises a set of electrodes having the ability to be implanted in excitable tissue of a patient, a stimulation device connected to said set of electrodes and having the ability to stimulate said excitable tissue via said set of electrodes, a first computer program connected to the stimulation device and having the ability to transform information provided by the patient to an assigned value for a tested group of electrodes, to calculate a total assigned value for each electrode, and to choose a preferred set of electrodes to be used for stimulation treatment.

In a fifth aspect the present invention refers to a method for optimization of the stimulation specificity and the energy consumption of implanted electrodes in excitable tissue of a patient, wherein it comprises the step of electrical stimulation of excitable tissue between one or more combinations of electrode pairs in a cluster of electrodes, optionally comprising the electrodes chosen to be included in a stimulation pattern according to the first aspect, or electrical stimulation between one or more combinations of electrode pairs in two or more clusters of electrodes, wherein the two electrodes of said electrode pairs do not belong to the same cluster, wherein said two or more clusters of electrodes optionally comprises the electrodes chosen to be included in a stimulation pattern according to the first aspect, wherein the electrical stimulation between different combinations of electrode pairs in a cluster of electrodes, or the electrical stimulation between different combinations of electrode pairs in two or more clusters of electrodes, creates a directed electrical field; wherein the effect of the directed electrical field is assessed after each stimulation step by registering information provided from the patient in view of a therapeutic effect and by monitoring the energy consumption, followed by choosing the electrode pair or pairs which give rise to the lowest energy consumption while still giving a therapeutic effect, or assigning each electrode pair a value related to said information provided by the patient and the energy consumption; and choosing the electrode pair or pairs which give(s) rise to the most favorable assigned value.

DETAILED DESCRIPTION OF NON-LIMITING EMBODIMENTS

Figure 1:
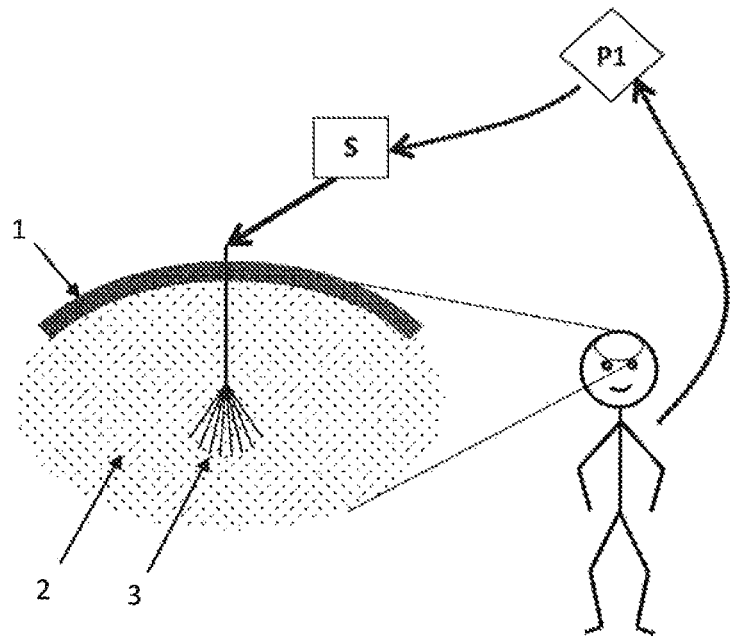
FIG. 1 schematically shows a system according to the present invention comprising a first computer program P1 and a stimulation device S which is capable of stimulating electrodes 3 implanted in excitable tissue 2 of a human or an animal.

First, some specific expressions and terms used throughout the application text will be defined.

The expression "optimization of the stimulation pattern of a set of implanted electrodes" is to be understood as finding a satisfactory stimulation pattern. The found stimulation pattern need not be the best theoretical pattern, but rather a "good enough" pattern. The word "optimal" is to be understood in accordance with the above.

Endocrine tissue or endocrine organs are tissues or organs which secrete hormones into the circulation.

A "nucleus" (plural nuclei) is an anatomically defined cluster of neurons, e.g. the subthalamic nucleus, nucleus habenula etc. The wording nucleus should not limit the use.

"Anatomical compartment" is defined as a structure that is delineated anatomically, for example the thalamus, cortex cerebri, the subthalamic nuclei, and the dorsal horn of the spinal cord.

A "subnucleus" is defined as a subcompartment of a nucleus, such as the ventroposterior nucleus or ventromedial nucleus of thalamus or part of the ventroposterior nucleus involved in face somatosensory functions.

An "activity pattern" is defined as a discharge pattern of neurons. The activity pattern may be measured as action potentials and/or local field potentials.

"Search field" is defined as a predetermined subgroup of electrodes or subgroup of stimulation parameters for a given group of electrodes. In some embodiments, "search field" may be defined as including all electrodes.

All electrodes are stimulated against a reference electrode, unless otherwise stated. The reference electrode may be placed outside the stimulated area, unless otherwise stated. The reference electrode should have a low impedance to reduce energy consumption during stimulation.

"Electrode" is defined as an implanted lead including the non-insulated part where current from the stimulator can be passed into the tissue.

According to the above defined first aspect of the invention, the above and other objects of the invention are achieved, in full or at least in part, by the method as defined in the independent method claim.

When implanting a larger number of electrodes into excitable tissue, e.g. neuronal tissue, it is most likely that some of the implanted electrodes give rise to no effect or to negative effects when used for stimulation of the neuronal tissue. It is also most likely that stimulation of a combination of electrodes will give the best effect, i.e. decreased or abolished symptoms with as few negative effects as possible. The method according to the present invention may be used to find such an optimal combination of electrodes. In addition, the method according to the present invention may also be used to find optimal stimulation parameters for each electrode in the combination.

The present invention provides a method for finding the optimal set of electrodes for stimulation as well as a method to reduce the number of electrodes needed to obtain a satisfactory result.

The stimulation of the targeted tissue does preferably not start until the patient actively instructs the system to do so. Thus, the patient is given full control over the situation.

The time period under which stimulation occurs may be set in advance.

The time period between different stimulations may be set in advance.

Each electrode may be included in one or several tested groups.

The number of electrodes included in each group is dependent on the total number of implanted electrodes. Preferably, 3-15 electrodes are included in each group. Typically, 20% of the total number implanted electrodes are used in each group which is used for stimulation. Every single electrode may be tested at least 3 times, preferably at least 5 times, more preferably at least 10 times, most preferably at least 12-15 times. Every single electrode may be tested even more times.

Generally, the stimulation is carried out at 0.1-5 V, preferably below 2 V and occasionally as high as at 10 V.

Each test stimulation comprises a train of electrical pulses. Each pulse in the train may be longer than 2 ms. The internal frequency of stimulation pulses may exceed 50 Hz. Each test stimulation may have a duration of at least 100 ms, preferably at least 1 s, or most preferably at least 5 s.

Each pulse is preferably balanced with respect to the charge emitted from the electrode. For example, a symmetric biphasic square wave which initially has a negative potential followed by a positive potential. Other wave shapes are within the scope of the invention.

The total assigned value for each electrode may be calculated as the sum of all values assigned to the electrode. Median values are preferred when the sample size is small, such as for samples less than 7 tests.

Alternatively, the total assigned value for each electrode may be calculated as the average value of all values assigned to the electrode.

The total assigned value for each electrode may be calculated as the median value of all values assigned to the electrode.

The predetermined value involved in the method according to the present invention is determined depending on the scale used. E.g., a symmetric scale covering the span from −100 to +100 may be used, wherein −100 indicates maximal adverse effects and +100 indicates total relief of symptoms. The threshold may then be >0, i.e. when the electrode adds positively to the therapy. Alternatively, the threshold may be set to >30 by the reason that the placebo effect normally appears in that region and that a symptom release of at least 30% is desirable if the treatment is to be competitive. In certain applications, the threshold may be set to >50. Said value obtained for each group of electrodes is assigned on a digital or analog scale, wherein values on one side of the midpoint correspond to therapeutic effect and values on the other side of the midpoint correspond to adverse effects. In other applications, e.g. when a visual analog scale is used, 0 is to the right and 100 to the left. Usually 0 means no pain and 100 is maximal pain. Thus, in this case the best values are to the right.

The total assigned value for each electrode may be calculated as the sum of all values assigned to the electrode. This requires that each electrode has been stimulated the same number of times.

Alternatively, the total assigned value for each electrode may be calculated as the average value of all values assigned to the electrode.

The total assigned value for each electrode may be calculated as the median value of all values assigned to the electrode. The total assigned value for each electrode may in one embodiment be the sum of a component describing the effect of the stimulation on the symptoms which are to be treated and of a component describing any side effects of the stimulations.

The total assigned value for each electrode may be comprised of a component describing the effect of the stimulation on the symptoms which are to be treated and a YES or NO regarding the side effects of the stimulations.

Combinations of the above-mentioned ways to calculate the total assigned value may be utilized in one embodiment.

If one specific electrode is associated with a negative effect in all or in a majority of the tests, such as a low degree of effect on the condition or disease which is treated, or such as a side effect, the groups may be tested again without this specific electrode.

One advantage of the current invention is that, through this method, electrodes which give rise to the desired therapeutic effect may be found in a time efficient manner. In addition, electrodes the stimulation of which give rise to undesired effects may be identified in a time efficient manner and may thus be excluded from the used set of electrodes.

The time needed to find electrodes which give rise to the desired therapeutic effect depends on how often the test pulses may be given and the time needed to evaluate each test. For example, if the effect of the stimulation is immediate, each test cycle may take about 30 s. The test cycle includes the feedback provided by the patient. Thus, if the effect of the stimulation has a long onset time, the evaluation of each test cycle is prolonged.

The interval between test cycles is influenced for example by the duration of the effect, i.e. the time for return of the symptoms. For DBS in treatment of Parkinson's disease both onset latency and duration is relatively short, typically less than one minute.

For example, if the effect of 30 electrodes is to be evaluated, and 20% of the electrodes are tested in each test cycle, and each electrode is to be tested 10 times, a total number of 50 test cycles must be performed. If each test cycle takes 1 min, the electrodes which give rise to the desired therapeutic effect may be found in 50 min. If each of the 30 electrodes were to be tested individually, it would take 300 min to find the electrodes which give rise to the desired therapeutic effect.

Another advantage is that combinations of electrodes which give rise to the desired therapeutic effect may be found.

The method according to the present invention may be used for optimization of the stimulation pattern of a set of implanted electrodes in order to treat and/or alleviate Parkinson's disease.

The method may be used for optimization of the stimulation pattern of a set of implanted electrodes in order to treat and/or alleviate pain. The pain may be chronic pain. The pain may be neuropathic pain.

The method may be used for optimization of the stimulation pattern of a set of implanted electrodes in order to treat and/or alleviate emotional disorders, e.g. depression and anxiety.

The method may be used for optimization of the stimulation pattern of a set of implanted electrodes in order to treat and/or alleviate epilepsy.

The method may be used for optimization of the stimulation pattern of a set of implanted electrodes in order to treat and/or alleviate conditions involving delusions.

The method may be used for optimization of the stimulation pattern of a set of implanted electrodes in order to treat and/or alleviate psychological disorders, e.g. Tourette's syndrome and obsessive compulsive disorder (OCD).

The method may be used for optimization of the stimulation pattern of a set of implanted electrodes in order to treat and/or alleviate eating disorders, e.g. anorexia nervosa and bulimia.

The method may be used for optimization of the stimulation pattern of a set of implanted electrodes in order to treat and/or alleviate obesity.

The method may be used for optimization of the stimulation pattern of a set of implanted electrodes in order to treat and/or alleviate cognitive disorders, e.g. Alzheimer's disease.

The method may be used for optimization of the stimulation pattern of a set of implanted electrodes in order to treat and/or alleviate sleep disorders, e.g. narcolepsy.

The method may be used for optimization of the stimulation pattern of a set of implanted electrodes in order to treat and/or alleviate high blood pressure.

The method may be used for optimization of the stimulation pattern of a set of implanted electrodes in order to regulate the body temperature.

The method may be used for optimization of the stimulation pattern of a set of implanted electrodes in order to regulate circadian rhythms.

The method may be used for optimization of the stimulation pattern of a set of implanted electrodes in order to regulate the biological clock of a patient.

The patient may be a human or an animal, and e.g. chronic pain or aggression in pets may be treated.

According to one embodiment of the present invention, the method may be preceded by a step of stimulating all electrodes at the same time while increasing the stimulation strength. Threshold(s) for adequate therapeutic effects and significant adverse effects can thus be established and used in the search routine above, more precisely for use in the step of stimulating the excitable tissue.

Stimulation strength may be amplitude in voltage or in current.

For example, the thresholds for adequate therapeutic effects can then be used when searching for effective sub-groups as above. One advantage of this embodiment is that the patient is gradually acquainted to the effect of stimulation. Another advantage is that a stimulation strength is established, which is used in the following steps. This minimizes the risk of stimulating with a too high strength which could lead to serious negative effects.

Energy saving is one aim since this prolongs the battery endurance but does not necessarily result in impaired therapy. Reducing the group of implanted electrodes to a sub-group of electrodes which are used for stimulation still providing satisfactory results will significantly reduce the energy expenditure.

The invention is based on the insight that reducing the energy consumption by using a sub-selection of electrodes which produce acceptable results will also often increase the specificity of the stimulation and reduce the incidence of side effects by avoiding stimulation of electrodes or stimulation intensities that produce undesired results.

Thus, as disclosed above, a second aspect of the present invention refers to a method for optimization of the stimulation pattern which is carried out as two separate optimizations. The first optimization comprises the steps of choosing a first group of a certain number of electrodes from said set of implanted electrodes, stimulating the excitable tissue electrically by said first group of electrodes, registering information provided by the patient, assigning each electrode of said first group of electrodes a value related to said information, and wherein the method is repeated for one or more further groups of said certain number of electrodes chosen from said set of implanted electrodes, wherein each electrode may be included in one or several groups, wherein the total assigned value for each electrode is calculated, and wherein electrodes having a total assigned value exceeding a predetermined value are chosen for a group of electrodes to be included in said stimulation pattern. The subsequent second optimization is an optimization of stimulation parameters for the electrodes chosen to be included in said stimulation pattern according to claim 1 in view of the energy consumption needed for said chosen electrodes to give rise to a therapeutic effect, wherein the second optimization comprises the steps of varying one or more of the stimulation parameters for said chosen electrodes in a stimulation test series; registering information provided by the patient; monitoring the energy consumption for each stimulation test where the stimulation gives rise to a therapeutic effect; and choosing, as the stimulation parameters, the parameters which give rise to the lowest energy consumption while still giving a therapeutic effect; or assigning each stimulation test a value related to said information provided by the patient and the energy consumption; and choosing the parameters which give rise to the most favorable assigned value.

The parameters which may be varied comprise the pulse width, the amplitude of the stimulation pulse, the stimulation strength, the stimulation frequency, the shape of the stimulation pulse, the polarity, the stimulation type as to the degree of randomization and the temporal pattern of stimulation, e.g. periods of higher frequency followed by lower frequencies or quiescence as when burst stimulation is used, wherein the internal frequency of pulses in the burst is higher than the frequency of the bursts. One example is to use bursts with 3-10 pulses at an internal frequency exceeding 200 Hz, wherein the bursts are separated by a period of less frequent stimulation. Another pattern is to use amplitude modulation or frequency modulation. In the first case amplitude modulation means that the pulse amplitude is varied over a certain time cycle between defined values. Frequency modulation means that the frequency is varied in same way. The modulation may be e.g. sinusoidal variation of pulse amplitude or frequency.

Alternatively, a first group of electrodes in the first optimization step is assigned a value based on the information provided by the patient and the energy consumption needed to give rise to a therapeutic effect.

Each group of electrodes may be tested several times, but with different stimulation parameters. The parameters which may be varied comprise the pulse width, the amplitude of the stimulation pulse, the stimulation strength, the stimulation frequency, the temporal pattern of stimulation, the shape of the stimulation pulse, the polarity, and the stimulation type as to the degree of randomization.

The assigned value may be a function of the therapeutic effect induced by stimulation by the electrode group and of the energy consumption needed. In this way, the energy consumption may be optimized at the same time as a therapeutic effect is ensured.

Alternatively, the assigned value will be a weighted function. For example, the therapeutic effect and the energy consumption are given the same weight. Another example is that the weight of the energy consumption is dependent on the effect which is reached and grows in importance above a therapeutic threshold (good enough).

In the case when the assigned value is based on the information provided by the patient and the energy consumption needed to give rise to a therapeutic effect, the function may include threshold values for the effect and/or the energy consumption such that a value is assigned only when the therapeutic effect is above a certain predetermined value and when the energy consumption is below a certain predetermined value.

Alternatively, the first optimization step is preceded by a step of initially stimulating all electrodes while stepwise increasing the stimulation strength. As stated above, one advantage of this embodiment is that the patient is gradually acquainted to the effect of stimulation. Another advantage is that a stimulation strength is established, which is used in the following steps. This minimizes the risk of stimulating with a too high strength which could lead to serious negative effects, such as pain, panic, vertigo, speech problems, and emotional disturbances such as aggression. The patient assigns a therapeutic value to each step and notes the occurrence of adverse effects. In this way an overall view is initially created. It may be that no adverse effect is encountered. If so, the method above may be used to fine tune the energy consumption.

According to one embodiment of the invention, the set of implanted electrodes comprises a plurality of microelectrodes. In this context, a microelectrode is defined as electrodes having a diameter of less than 100 μm, i.e. the lead has a diameter of less than 100 μm. However, active sites in the electrode may have a diameter larger than 100 μm. The length of the electrode may be of any length suitable for the target. The part of the electrode used to emit current to the tissue (usually the non-insulated part of the electrode) is not limited in size.

According to another embodiment of the invention, the electrodes may be larger, such as e.g. electrodes used for spinal cord stimulation.

Compared to conventional electrodes used for e.g. DBS (typically about 1 mm) in diameter, an individual electrode in a microelectrode is very small and can thus be very specific regarding the neuronal tissue which it stimulates. This depends on how large the active surface is. In some cases, such an electrode can be regarded as stimulating only the most adjacent cells. This gives the possibility to tailor the stimulation pattern and parameters to the individual patient and to decrease the negative effects that stimulation of some cells or groups of nearby cells give rise to. Such negative effects may be hallucinations, discomfort such as nausea, anxiety, aggression, or other emotional disturbances.

One advantage of microelectrodes is that such small electrodes, due to their smaller size, may be integrated into nerve cell circuits better than a larger electrode. This is especially important since e.g. specific stimulation within sub-compartments in a tissue volume of less than approximately 1 mm3 requires microelectrodes that are much smaller than conventional electrodes for DBS, which are in the mm scale.

Another advantage is that microelectrodes, due to their smaller size, usually are much more biocompatible than larger electrodes (Thelin J, Jörntell H, Psouni E, Garwics M, Schouenborg J, Danielsen N, Linsmeier C E. Implant size and fixation mode strongly influence tissue reactions in the CNS. PLoS One. 2011 Jan. 26; 6(1)e16267). Thus, such electrodes give rise to less glial scarring, reducing the problem of having to increase the current intensities to achieve neural stimulation. The problem with glial scarring is that it increases the distance from the electrodes to viable neurons.

According to a further embodiment, the set of implanted electrodes comprises electrodes which have active sites for charge ejection located on different physical entities. Examples of such electrodes are electrode arrays or electrode bundles in which several individual electrodes together make up the probe (Lind G, Linsmeier C E, Thelin J, Schouenborg J, Gelatine-embedded electrodes—a novel biocompatible vehicle allowing implantation of highly flexible microelectrodes. J Neural Eng. 201 August; 7(4): 046005. Epub 201 June 16). In other words, the electrodes or active sites are physically separated in target tissue. In this context, "active site for charge ejection" is the location on an electrode from where most of the stimulation is transferred to the surrounding tissue.

An advantage of such electrodes is that they, since they are located on different physical entities, can be spread throughout the tissue which is to be stimulated or spread on the border of the tissue which is to be stimulated and thus can limit the stimulated volume necessary for achieving therapeutic effects.

Importantly, stimulation between pairs or groups of electrodes in the implanted array or bundle of electrodes can be used to direct the stimulation field within a cluster of electrodes. The electrical field is focused between the electrodes used, and the current distribution is dependent on the resistance of the tissue. Current taking a detour between two electrodes becomes reduced, and thereby the current is focused to the area between the electrodes. If electrodes present in the periphery of the electrode cluster are used as a pole, a sub-group of the electrodes present within the cluster may be used as an opposite pole.

Neurons and in particular their axons are often oriented along a main axis. For example, the dendrites of "pyramid" neurons in cortex cerebri extend toward the surface of the cortex. Such neurons therefore are oriented to some extent along an axis that is parallel to the normal of the cortical surface. Another example of polarized neuronal structures is neuronal pathways comprising axons connecting different regions in the brain or spinal cord. The white matter of the central nervous system comprises a large number of axons often running in more or less parallel bundles. While for most parts the axis parallel to the bundles change little in orientation, the direction of the axons may change direction along its path, such as when corticospinal pathways cross the midline in the medulla. An additional example is peripheral nerves which comprise multiple axons extending in the same main direction but close to the spinal cord may deviate from the main axis.

To initiate nerve impulses (action potentials) with electric stimulation of a neuron, the membrane potential of cell body or its axon has to become depolarized to the threshold of the action potential. For this to happen during electrical stimulation, current has to pass into the cell in one area of the cell (which gets depolarized) and out from the cell in other areas (which gets hyperpolarized). Therefore, to initiate a nerve impulse in a neuron, an electrical field directed along the main axis of the neuron is usually more effective (requires less current) than an electrical field directed transverse to the main axis of the neuron (Kandel, E. R. Schwartz, J. H. and Jessell, T. M. (2000) Principal of Neural Science, Fourth edition, McGraw-Hill Companies, Inc, New York, London, Tokyo, 1414 pages).

The present invention is based on the insight that stimulation between pairs or groups of electrodes spread out in the tissue can be used to direct the electrical field within a cluster of electrodes. The direction of the electrical field is here defined as the main direction of current between the electrodes within the cluster of electrodes. In case the electrodes are divided into two groups wherein each electrode of respective group has same potential the main current direction will be from the group with positive potential to the group with negative potential.

The disclosed invention is based on the insight that the electrical field can be directed in different ways by stimulating between different electrodes or groups of electrodes in a cluster of electrodes spread out in the excitable tissue, and that this can be used to increase the specificity of the stimulation and to reduce the energy consumption of the treatment.

In one embodiment of the invention, the positions of the individual implanted electrodes spread out in the tissue are determined using imaging techniques such as computer tomography. Stimulation is preferably made either between electrodes from which therapeutic effects have been obtained or between the electrodes that do not give rise to adverse effects as described above.

In another embodiment, the electrodes of the electrode pairs are positioned in two different electrode clusters located close to neurons occupying two separate hemispheres of tissue or in such a way that the electrical field obtained is directed along the main axis of neurons.

In yet another embodiment, wherein it is combined with the second optimization as defined above.

In one embodiment, one single electrode forms pairs with two or more other electrodes.

In another embodiment, several pairs of electrodes are used for stimulation at the same time.

In another embodiment, one chosen pair of electrodes is used for stimulation consecutively after another pair of electrodes has been used for stimulation. In this way, a "wave" of stimulation may be achieved.

In one embodiment of the present invention, the implanted electrodes are divided into two groups between which stimulation is made. In case the position of the electrodes is known with respect to each other, stimulation can be applied between groups of neurons occupying two separate hemispheres of tissue such that current passed from each electrode will add to the current in the main direction from one group to the other. By systematically exchanging electrodes between the two groups, the effect of different directions of the electrical field can be assessed with respect to the therapeutic effects and energy consumption and the direction that produces an acceptable therapeutic effect with the lowest energy consumption can be determined. Alternatively, the combination causing an optimal therapeutic effect at an acceptable energy expenditure is determined. Stimulation strength, frequency, pulse shape and duration are preferably held constant while searching for the optimal direction of the electrical field.

In another embodiment, structural data is obtained on the orientation of nearby cells and axons from anatomical descriptions of the region of interest. By combining the structural data and data on the location of the active sites of the implanted electrodes, the two groups of electrodes that can be predicted to produce the most promising direction of the electrical field may be evaluated first in order to reduce the time to find a therapeutic effect.

Optionally, data on preferred direction of the applied electrical field in same tissue in previous patients stored in a database is used to assign the electrodes to either of group 1 or group 2 such that stimulation between the groups of electrodes results in the predetermined main direction of the electrical field to be tested. The therapeutic effect and energy consumption for the tested orientation of the electrical field is stored in a data base. Since, as described above, there are inter-individual differences between patients and the electrodes will not likely occupy identical sites in different patients it may be necessary to fine tune the direction of the electrical field by reassigning some of the electrodes in the first of the two group to the second group and vice versa to find the optimal assignment of electrodes into the two groups of electrodes. Stimulation strength, frequency, pulse shape and duration are preferably held constant while searching for the optimal direction of the electrical field.

According to a further embodiment, the set of implanted electrodes comprises electrodes which are located on the same physical entity. The entity has e.g. a rod-like shape. The entity may be a foil. The entity may be non-soluble or non-degradeable.

Importantly, an embodiment wherein a directed electrical field is used for stimulation may include one or more of the features discussed in this application.

Furthermore, an embodiment wherein a directed electrical field is used for stimulation may be used to treat one or more of the medical conditions discussed in this application.

According to one embodiment of the invention, the excitable tissue may be neuronal tissue or endocrine tissue, the heart or the vascular system. The tissue may be human or animal tissue.

According to another embodiment of the invention, the neuronal tissue may be brain tissue, spinal cord or peripheral nerves.

Importantly, the present invention applies to grey and white matter in the brain and spinal cord, as well as to peripheral nerves. This applies to both electrodes implanted in target tissue as well as electrodes implanted on the surface or nearby the target tissue, e.g. conventional electrodes used for spinal cord stimulation.

According to yet another embodiment of the invention, the brain tissue may be selected from the group consisting of e.g. subthalamic nucleus (STN), globus pallidus interna (GPi), periaqueductal grey substance, periventricular grey, internal capsule, ventral posterolateral nucleus, thalamus, striatum, habenula, hypothalamus, basal nucleus of Meynert, cortical areas, brain stem, medial forebrain bundle, internal capsule, amygdala, hippocampus, septum, and ventral posteromedial nucleus. However, it is important to realize that any brain tissue may be stimulated and thus the present invention may be used to optimize the stimulation of these tissues.

The subthalamic nucleus (STN) and globus pallidus interna (GPi) are commonly used sites for DBS treatment of Parkinson's disease. However, other sites, such as the caudal zona incerta and the pallidofugal fibers medial to the STN, locomotor regions in the brain stem may also be stimulated in the treatment of Parkinson's disease.

In the case where the stimulation of brain tissue is for treating and/or alleviating nociceptive pain, the brain tissue may be structures that are involved in pain modulation. Examples of such structures are the periaqueductal grey substance, thalamus, brain stem structures such as locus coerulius, raphe nuclei, cerebellum, dorsal column of the spinal cord, dorsal root ganglia, nucleus habenula, and periventricular grey.

In the case where the stimulation of brain tissue is for treating and/or alleviating neuropathic pain, the brain tissue may be the internal capsule, ventral posterolateral nucleus, and ventral posteromedial nucleus.

The present invention may be used to optimize the stimulation of any electrically excitable tissue, e.g. peripheral nerves and innervated targets.

Thus, the present invention may be used to optimize the stimulation of the electrical conduction system of the heart, e.g. for the optimization of the stimulation by a pacemaker. Furthermore, the present invention may be used to find a subset of electrodes causing the lowest energy consumption for effective and reliable use in pacemaker therapy.

The present invention also applies to endocrine organs.

According to one embodiment of the invention, the endocrine tissue may be selected from the group comprising pancreas, pituitary gland, and pineal gland.

Pancreatic tissue may be stimulated to treat and/or alleviate e.g. diabetes.

Thus, another example is to find the most effective way of regulating insulin production by selecting nerve fibers causing an increased gain (in the relation between insulin production to blood glucose levels, which is typically lowered in diabetes type 2) in the B-cells in the Langerhan's islet cells in the pancreas. In this example the signal from the patient should involve glucose measurements in order to assess the stimulation produced change in sensitivity (gain). It is known that one of the functions of the vagus nerve is to mediate central commands regulating the sensitivity in these endocrine cells. Since the vagus nerve is involved in regulation of many organs, via different nerve fibers, it is an advantage to improve the selection of nerve fibers stimulated to those related to the disease treated. By implanting many electrodes in and around the vagus nerve, optionally in the pancreas itself, and then selecting the electrodes producing an increase in glucose sensitivity in the B-cells in the Langerhan's islet cells in the pancreas (i.e. increased gain in the relation between insulin production and blood glucose levels), which is typically lowered in diabetes type 2. Note that in this example the signal from the patient should involve glucose measurements in order to assess the stimulation produced change in sensitivity (gain).

The pituitary gland and hypothalamus may be stimulated to treat and/or alleviate e.g. blood pressure and body growth.

There are a number of other applications in the body where an advantageous strategy could be to spread out biocompatible electrodes in and around the target and then select the most appropriate electrodes to reach therapeutic effects and/or save energy.

According to another embodiment, each group of electrodes is chosen randomly. One advantage of this embodiment is that each electrode is tested together with other electrodes which are randomly chosen. In this way, unexpected effects relating to the concomitant stimulation of two or more electrodes may be found.

Preferably, electrode groups may be used, in which the relative location of the individual electrodes are known, such that it is known that the electrodes which are located close to electrode X are electrodes Y, Z and W. This enables that the effect of stimulation within limited locations may be systematically explored, thus reducing the time needed to find electrodes which give rise to the desired therapeutic effect, as compared to when the local distribution of the electrodes is unknown.

According to another embodiment, each group of electrodes is chosen by performing the following steps of recording of an activity pattern in the excitable tissue by each implanted electrode, optionally identifying the anatomical compartment or type of cells from which the electrode is recording the activity pattern, comparing the recorded activity pattern with information stored in a database, and choosing the group of electrodes to be used for stimulation on the basis of a result of said step of comparing and/or optionally on the basis of the identified anatomical compartment.

The information stored in the database may comprise activity patterns coupled to the effect of stimulating cells or groups of cells which exhibit the activity pattern. The information in the database may have been collected from many different patients, e.g. up to more than 1000 patients. The activity patterns may be 2D diagrams where the neuronal discharge frequency and time is presented on the X and Y axis, respectively. The effect of stimulation may be given on a scale from −100 to +100, where +100 signifies maximal therapeutic effect and −100 maximal side effects, as disclosed above.

An advantage of this embodiment is that by using the database to predict the electrodes which are most likely to give rise to the desired therapeutic effect when they are used for stimulation, a limited number of electrodes may be used for the optimization of the final stimulation pattern. Preferably, the electrodes used for registration are not used for stimulation. The electrodes used for registration provide information regarding the anatomical locations in the target area that is to be stimulated. Thus, according to one embodiment of the invention, stimulation is made through electrodes nearby the recording electrodes that show the most promising activity pattern(s).

According to yet another embodiment of the invention, each group of electrodes is chosen by performing the following steps of recording of an activity pattern in the excitable tissue by each implanted electrode, optionally identifying the anatomical compartment or type of cells from which the electrode is recording the activity pattern, and choosing the group of electrodes to be used for stimulation on the basis of the recorded activity patterns and/or optionally on the basis of the identified anatomical compartment.

It is well known that different cells or groups of cells (anatomical compartments) have different activity patterns. Different anatomical compartments have different characteristics and implications and consequently play different roles in different diseases and disorders. By choosing the groups to be tested based on the assumed role and potential implication of a certain anatomical compartment in the treatment of a certain disease, the time used for the optimization of the stimulation pattern of the set of implanted electrodes may be shortened. In addition, by using the database to predict the electrodes which are most likely to give rise to the desired therapeutic effect when they are used for stimulation, a limited number of electrodes may be used for the optimization of the final stimulation pattern.

According to a further embodiment of the present invention, the method further comprises the following steps of coupling the anatomical compartment or type of cells with the information from the patient in a database, and coupling combinations of electrodes which stimulate certain anatomical compartments or types of cells to the information from the patient in a database. The documentation with respect to anatomical compartments can be done using e.g. CT or MRI imaging.

In this way, a database is established comprising information regarding the anatomical compartments or types of cells and information about the effect of stimulation of the anatomical compartments or types of cells. The database may also comprise information about e.g. energy consumption and effective stimulation parameters such as e.g. frequency, amplitude and wave shape. The database may later be used when determining the groups which are to be tested when optimizing the stimulation pattern of a set of implanted electrodes in a new patient. The information stored in the database may comprise activity patterns coupled to the effect of stimulating cells or groups of cells which exhibit the activity pattern. The information in the database may have been collected from many different patients, e.g. up to more than 1000 patients.

According to another embodiment of the invention, the method according to the present invention may also comprise the step of optimizing one or more stimulation parameters for the use of the electrodes chosen to be included in the stimulation pattern in a stimulation treatment of the patient, wherein said chosen electrodes are subjected to stimulation tests in which one or more stimulation parameters chosen from the group comprising the pulse width, the amplitude of the stimulation pulse, the stimulation strength, the stimulation frequency, the temporal pattern of stimulation, the shape of the stimulation pulse, the polarity, and the stimulation type as to the degree of randomization, amplitude modulation, frequency modulation are varied wherein information provided by the patient is registered for each test, wherein each parameter set is assigned a value related to said information, and wherein the parameter set having the most favorable assigned value, e.g. on the above-mentioned scale from −100 to +100 is chosen to be used for the chosen electrodes during the stimulation treatment, or wherein said one or more stimulation parameters also are used in the stimulation test of the second optimization step in view of energy consumption.

The stimulation strength influences the number of nerve cells in the vicinity of the stimulated electrode, and the frequency influences the impulse frequency of the nerve cells.

Optionally, one or more parameters may be held constant while the other parameters are varied. In one example the frequency is stabilized at 150 Hz and the pulse duration at 200 µs, while varying the amplitude of the stimulation pulses from 0.1 to 10 volts.

According to another embodiment, said step of optimizing one or more stimulation parameters also or alternatively is performed for one or more of the groups of electrodes, preferably all of the groups of electrodes, chosen from said certain number of electrodes from said set of implanted electrodes.

According to another embodiment of the invention, the method according to the present invention may also comprise the step of optimizing one or more stimulation parameters for the use of the electrodes chosen to be included in the stimulation pattern in a stimulation treatment of the patient, wherein said chosen electrodes are subjected to stimulation tests in which the burst mode, is varied wherein information provided by the patient is registered for each test, wherein each parameter set is assigned a value related to said information, and wherein the parameter set having the most favorable assigned value is chosen to be used for the chosen electrodes during the stimulation treatment, or wherein said one or more stimulation parameters also are used in the stimulation test of the second optimization step in view of energy consumption according to claim 3.

According to another embodiment of the invention, one or more of the amplitude of the stimulation pulse, the stimulation frequency, and the shape of the stimulation pulse may be varied in each test.

According to another embodiment of the invention, each group of electrodes is chosen by performing the following steps of performing brain scanning, MRI examination, CT examination, and/or ultrasound examination, identifying the anatomical compartments where the electrode is located, and choosing the group of electrodes on the basis of the location of the electrodes.

By choosing the electrodes which are to be tested on the basis of their physical location as determined by a brain scan, an MRI examination, a CT examination and/or an ultrasound examination, the time used for the optimization of the stimulation pattern of the set of implanted electrodes may be shortened.

According to one embodiment of the invention, the number of electrodes in each group is 1-15, preferably 5-15. However, the number of electrodes included in each group may be dependent on the total number of implanted electrodes, such that up to 50%, preferably 15-30%, more preferably 20-25%, of the implanted electrodes are included in each group. The number of electrodes included in each group may also be all implanted electrodes except one or more.

According to another embodiment of the invention, the information from the patient is a response to the effect of the stimulation perceived by the patient. Such effects may be related to anxiety, nausea, vertigo, dizziness, itch, anger, tiredness, and sleepiness.

This is especially advantageous, since it is the patient's actual perception of the stimulation that guides the selection of electrodes which are to be used in the treatment. In this way, the patient can actively take part in the selection of electrodes, which will be more time efficient. Further, the patient will also feel that he/she has more control of the test protocol of the test procedure, which may relieve anxiety.

The information may be feedback actively given by the patient in view of a perceptual change of the patient's condition induced by the electrical stimulation.

According to another embodiment of the invention, the information from the patient is a value obtained by measuring a physiological, psychological, or pathological reaction of the patient. Examples of such reactions are e.g. blood pressure, blood glucose level, transpiration, muscle activity, eye movements, and body movements.

In certain cases, it may be more advantageous to use a measurement of a physiological, psychological, or pathological reaction of the patient in order to achieve a more favorable selection of electrodes which are to be used for the treatment. Such cases may be in patients who, due to their disorder, are unable to communicate their perceptions, such as for late stages of ALS, tetraplegic patients, severely depressed patients, and cognitively impaired patients. Other cases may involve conditions in which the effect of the stimulations is not perceived immediately by the patient, but in which the effect may be predicted by measuring a physiological, psychological, or pathological reaction of the patient, e.g. effects on depression can be deduced by tests measuring the response time, and memory impairments such as Alzheimer's disease can be tested using simple recognition tests.

According to another embodiment of the invention, the information from the patient is a combination of a response to the effect of the stimulation perceived by the patient and a value obtained by measuring a physiological, psychological, or pathological reaction of the patient.

According to one embodiment of the invention, the information from the patient may be binary. In such a case, the patient may indicate if the stimulation gives an effect or not.

The information from the patient may also be analogue or comparative, e.g. "better than before", "worse than before" or "same as before".

According to another embodiment of the invention, the information from the patient may be given on a scale. One example of such a scale is a "visual analogue scale" (VAS).

According to one embodiment of the present invention, 10-50, preferably 15-40, most preferably 20-35, different groups of electrodes are stimulated.

According to another embodiment, 3-50, preferably 10-40, most preferably 20-35, different groups of electrodes are stimulated.

According to one embodiment of the invention, the information from the patient may be provided by means of a joystick, a touch screen, a pad, a computer mouse, and/or a trackball. In this way, the method may be adapted to the patient's own possibilities to provide information about the effect of stimulation.

According to one embodiment of the invention, the information from the patient may be provided by means of a device registering eye movements. Especially, devices registering eye movements, so called "eye trackers", may be used. Such a device may be provided in special eyeglasses. With such a device even an almost paralyzed patient may be able to provide voluntary information about the effect of the stimulation by controlling e.g. a cursor on a screen.

According to another embodiment of the invention, the method steps may be preceded by a step in which the patient is allowed to get accustomed to the conditions and equipment utilized during the stimulation. After this step or "training period", the patient is accustomed to the device and to how it may be controlled. This is advantageous since the actual optimization will take less time than if the patient were not familiar with the procedure. In addition, the patient probably will feel more comfortable in the situation when the procedure is known beforehand.

The patient and a care provider, such as e.g. a physician, may be in one location when the optimization of the stimulation pattern of the set of implanted electrodes is performed, and may be in contact with an expert in the field who may be in another location. The expert may follow the procedure remotely, such as over the internet, and may provide guidance and comments.

According to one embodiment of the invention, the stimulation and the provision of information may be performed by the patient himself/herself via electronic connection with a practitioner/physician. Thus, a first optimization may be made under the supervision of a care provider and a fine tuning of the optimization may be made by the patient himself/herself, e.g. in his or her home. As the underlying disease conditions progress it may also be useful to tune the stimulation parameters over time. This may be advantageous since the patient need not leave his or her home to go to a hospital to do the fine tuning of the stimulation. In addition, for certain conditions, such as e.g. depression, the full effect of stimulation of excitable tissue is not seen until after several weeks, and it is thus favorable if a gradual fine tuning of the stimulation may be performed over a longer period of time by the patient in his or her home. This fine tuning may be performed under the supervision of a care provider, e.g. by contact via e.g. the internet. Thus, there is no need for the patient to leave his/her home in order to fine tune the stimulation. This procedure is also cost saving for the care provider. The fine tuning may be limited to certain electrodes, such that electrodes which were found to induce negative effects when stimulated are excluded from the fine tuning step. The fine tuning may be limited between certain stimulation parameters.

A care provider may have the possibility to terminate the stimulation if undesirable side effects occur.

In certain situations, a side effect may be diminished or abolished by fine tuning of the stimulation parameters, such as frequency, pulse shape, amplitude etc. Thus, if a side effect is detected, the stimulation parameters may be changed in order to maintain the positive effect on the symptoms of the treated disease or disorder, while the side effects are diminished or abolished.

According to one embodiment of the invention, the method may be followed on a screen device on which the implanted electrodes in the tissue are graphically represented, and wherein the patient has the ability to stepwise/gradually scan said groups of electrodes to stimulate the tissue. The electrodes may be graphically represented on e.g. a touch sensitive screen, The electrodes which are used for the current stimulation may be identified, e.g. by having a different colour, strength of the colour or by being denoted by a different symbol than electrodes which are not currently active. In this way, the location of the electrodes in the tissue is visualized. Thus, it may be easy to see already tested electrodes.

For blind patients auditory or somatosensory cues may be used instead to provide information on which electrodes are currently used.

Multivariate analysis may be used in order to identify which combinations of electrodes and/or which combinations of stimulation parameters give rise to the desired effect. In such a way, unexpected electrode combinations may be found.

According to a third aspect of the invention, the present invention relates to a method for treatment or alleviation of a disease or condition by use of a set of electrodes whose stimulation pattern has been optimized according to the method described above, wherein the disease or condition is chosen from the group consisting of brain and/or spinal damage, lost functions, pain, Parkinson's disease, tremor, motor disorders, choreatic and other involuntary movements, memory disorders, Alzheimer's disease, degenerative diseases, epilepsy, mood disorders, aggression, anxiety, phobia, affect, sexual over-activity, impotence, eating disorders, sleep disorders, such as narcolepsy, attention disorders, stroke, damage of the brain, damage of the spinal cord, bladder disorders after spinal cord injury, bowel disorders after spinal cord injury, spasticity, somatosensory disorders, auditory disorders, visual disorders, and olfactory disorders.

Neurons may be stimulated to compensate for lost functions. E.g. spinal neurons may be directly stimulated to trigger movements after lost connection with the brain or to trigger functions such as emptying of bladder or bowel.

Pain relief may be provided by stimulation of analgesic brain stem centers.

Relief or decrease of tremor and other motor symptoms in Parkinson's disease may be provided.

Relief or decrease of choreatic and other involuntary movements may be provided by stimulation within the basal ganglia or associated nuclei.

Memory may be boosted by stimulation of cholinergic and/or monoaminergic nuclei in case of Alzheimer's disease or another degenerative disease.

Control of mood, aggression, anxiety, phobia, affect, sexual over-activity, impotence, and eating disturbances may be provided by stimulation of limbic centres or other brain areas.

Sleep disorders may be treated by stimulation of suitable targets in thalamus and brain stem that regulate sleep.

Attention disorders may be treated by stimulation of locus coeruleus and other monoaminergic structures.

Rehabilitation after stroke or damage of the brain and/or the spinal cord may be provided by stimulation of remaining connections in the cortex cerebri, in the spinal cord, or in descending motor pathways.

Re-establishment of control of spinal functions such as bladder and bowel emptying after spinal cord injury, may be provided by stimulating relevant parts of the spinal cord or peripheral nerves.

Control of spasticity may be provided by stimulation of inhibitory supraspinal descending centers or appropriate cerebellar areas.

According to a fourth aspect of the present invention, a system for optimization of the stimulation pattern of a set of implanted electrodes in excitable tissue of a patient and for treatment or alleviation of a disease or disorder with the method according to the present invention is also provided. The system comprises a set of electrodes having the ability to be implanted in excitable tissue of a patient, a stimulation device connected to said set of electrodes and having the ability to stimulate said excitable tissue via said set of electrodes, a first computer program connected to the stimulation device and having the ability to transform information provided by the patient to an assigned value for a tested group of electrodes, to calculate a total assigned value for each electrode, and to choose a preferred set of electrodes to be used for stimulation treatment. The first computer program has the ability to choose a group of electrodes from the set of implanted electrodes and to instruct the stimulation device to stimulate the tissue through these electrodes. Alternatively, the first computer program has the ability to choose a set of nearby electrodes optimized for stimulation and to instruct the stimulation device to stimulate the tissue through these electrodes.

According to one embodiment of the invention, the system further comprises a recording device connected to said set of electrodes and having the ability to register an activity pattern in said excitable tissue, a second computer program connected to the recording device and to the first computer program, and a database connected to said first computer program and to said second computer program. The second computer program has the ability to compare information obtained from the recording device in view of the registered activity pattern in said excitable tissue with information in the database in the form of previously registered activity patterns for several patients regarding the effect of stimulation of the same or similar excitable tissue of said several patients, to choose a collection of useful electrodes with the basis on said comparison of activity patterns, and to transform the information about the chosen electrodes to the first computer program, wherein said first computer program also has the ability to transmit the information provided by the patient to the database for storage.

According to one embodiment of the invention, the set of implanted electrodes may comprise a plurality of microelectrodes.

According to another embodiment of the invention, the set of implanted electrodes may comprise electrodes which are located on different physical entities. Thus, the electrodes may be located on separate leads, i.e. they are not located on the same surface, plate or cylinder.

According to another embodiment of the invention, the system may further comprise a joystick, a touch screen, a pad, a computer mouse and/or a trackball, wherein the joystick, touch screen, pad, computer mouse and/or trackball is used by the patient to provide the first computer program with information.

According to one embodiment of the invention, the system may further comprise a device registering eye movements, wherein the device registering eye movements is used by the patient to provide the first computer program with information.

According to one embodiment of the invention, the system may further comprise a screen device on which the implanted electrodes in the tissue are graphically represented. The patient has the ability to stepwise/gradually scan said groups of electrodes to stimulate the tissue. This can be done by e.g. applying pressure on the symbols for the respective electrodes to be stimulated. The electrodes which are to be tested may be selected by moving a predetermined search field across a screen. The electrodes which are used for the current stimulation may be identified, e.g. by having a different colour, strength of the colour or by being denoted by a different symbol than electrodes which are not currently active. In this way, the location of the electrodes in the tissue is visualized. Thus, it may be easy to see already tested electrodes.

According to one embodiment of the invention, the system may further comprise conventional equipment for measuring the physiological reactions of the patients to the stimulation through the implanted electrodes. Such equipment includes but is not limited to electromyography (EMG) to record e.g. tremor, eye movements, involuntary movements, or voluntary movements, conventional equipment for measuring skin blood flow such as Laser Doppler techniques, conventional equipment for measuring blood pressure, equipment for measuring blood glucose levels, conventional multichannel equipment for electroencephalogram (EEG) to measure for example arousal, sleep cycles, brain states as defined by the frequency of the EEG, epileptic brain activity.

The system may be adapted to the patient regarding e.g. the speed and/or sensitivity of the device for controlling and/or providing the information. For example, if a patient has shaky hands or suffers from tremor, the sensitivity of the device may be set at a lower level so that only voluntary movements will be registered. In this way, overstimulation due to involuntary movements may be avoided. Further, a safety arrangement may be provided, by which the stimulation by the implanted electrodes is terminated if anything undesirable occurs during the stimulation, such as if the patient is affected by cramps, euphoria or other undesired side effects. Alternatively, or additionally, a care provider may have the possibility to terminate the stimulation if undesirable side effects occur.

The system may be provided with a history function, such that the patient and/or the care provider can identify which electrodes have already been tested. In addition, the history function may also show a representation of the results of the information provided by the patient.

The history function may be coupled to the screen, such that it is possible to visualize the electrodes which have been tested earlier during the procedure.

Selection of a preferred direction of the electrical field on stimulation can either be made by letting the computer systematically test the effect of different directions of the electrical field (accomplished as described above) while the patient provides feedback on the therapeutic effects as described above for the different parameters or the patient can by manipulating e.g. a joystick or button that can be turned clockwise or anticlockwise indicate the direction(s) causing the best therapeutic effects on a computer screen.

Optionally, the medically responsible person may operate the computer so as to scan through the different directions of the electrical field while the patient either indicates the therapeutic efficacy on a computer screen by moving a cursor or a joystick or in any other way as described above.

In cases where the patient is unable to indicate the therapeutic effect, a physiological measurement may be used instead as described above for assessments of the efficacy of different stimulation parameters.

The range of preferred directions of the electrical field is preferably stored in a data base along with data on selected electrodes and parameters of stimulation such as stimulation strength, pulse shape, frequency of stimulation, burst or tonic stimulation patterns and duration of stimulation.

By way of example, different embodiments of the present invention will now be described with reference to the accompanying drawings, in which:

FIG. 1 shows a system according to the present invention comprising a first computer program P1 and a stimulation device S which is capable of stimulating electrodes 3 implanted in excitable tissue 2 of a human or an animal. The stimulation may be performed synchronously or non-synchronously. Synchronous stimulation of all of the electrodes in a group means that an electric pulse reaches all the electrodes simultaneously. During non-synchronous stimulation the stimulation of the different electrodes does not take place simultaneously. One example is when the different electrodes in a group are consecutively stimulated during the test cycle. The first computer program P1 chooses a group of electrodes from the set of implanted electrodes 3 and instructs a stimulation device S to stimulate the tissue through these electrodes. A response from the patient is registered and this information is provided to the first computer program P1. The response provided from the patient is transformed by the first computer program P1 to a value which is assigned to all the electrodes of the group. This procedure is repeated for one or more different groups of electrodes from the set of implanted electrodes 3. When all groups have been tested, each individual electrode has been used for stimulation at least three times, preferably at least 10 times. The total assigned value is calculated for each electrode by the first computer program P1 and electrodes having a total assigned value exceeding a predetermined value are chosen to be included in the final stimulation pattern. The total assigned value may be an average value. The first computer program P1 provides the stimulation device S with the final stimulation pattern. Optionally, the first computer program can be externally controlled, via e.g. the internet.

Figure 2:
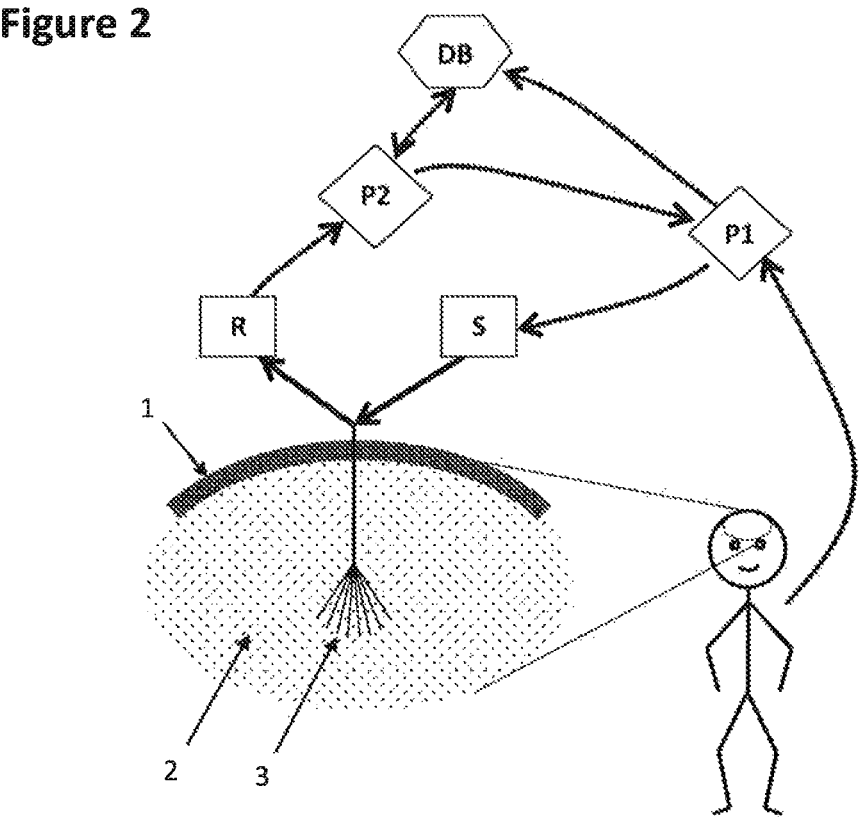
FIG. 2 schematically shows the system in FIG. 1, further comprising a registration device R, a second computer program P2, and a database DB.

FIG. 2 shows a system according to the present invention comprising a first computer program P1, a stimulation device S which is capable of stimulating electrodes 3 implanted in excitable tissue 2, a registration device R capable of registering signals transmitted from the excitable tissue 2 through the electrodes 3, a second computer program P2 and a database DB. The stimulation may be performed synchronously or non-synchronously. The registration device R records signals transmitted from the excitable tissue 2 through the electrodes 3 and provides a second computer program P2 with the information. The second computer program P2 compares the information received with information stored in the database DB. In the database DB information regarding previously recorded activity patterns from excitable tissue has been coupled with information regarding the effect of stimulation of the same tissue. In addition, the database may comprise data regarding the stimulation parameters, e.g. amplitude and frequency. Based on the recorded activity patterns and the information retrieved from the database DB, the second computer program P2 chooses a collection of electrodes and transmits this information to the first computer program P1. From the collection of electrodes the first computer program P1 chooses a group of electrodes from the set of implanted electrodes 3 and instructs a stimulation device S to stimulate the tissue through these electrodes.

A response from the patient is registered and this information is provided to the first computer program P1. The response provided from the patient is transformed by the first computer program P1 to a value which is assigned to all the electrodes of the group. This procedure is repeated for one or more different groups of electrodes from the set of implanted electrodes 3. When all groups have been tested, each individual electrode has been used for stimulation at least two times, preferably at least three times, most preferably at least 10 times. The total assigned value is calculated for each electrode by the first computer program P1 and electrodes having a total assigned value exceeding a predetermined value are chosen to be included in the final stimulation pattern. The total assigned value may be an average value. The first computer program P1 provides the stimulation device S with the final stimulation pattern. Optionally the first computer program can be externally controlled. Optionally, new information regarding the recorded activity pattern coupled to a response in the patient may be transmitted to the database DB and stored. The database may optionally also include stimulation data, such as values for different parameters. The computer program 1 and the computer program 2 may be the same computer program.

In the method and a system according to the present invention, mainly the patient is in charge and controls the events leading to the optimization of the stimulation pattern of a set of implanted electrodes in excitable tissue of the patient. Importantly, the method and system is user friendly, as mainly the patient has control by simple communication of stimulation effect to a computer. The system, by keeping track of the electrodes which have been stimulated and the outcome, greatly simplifies the task for the patient to optimize the stimulation when further fine tuning the stimulation parameters.

The method according to the present invention is performed on a set of electrodes which have been implanted in human or animal excitable tissue, neuronal tissue, e.g. the brain or the spinal cord, or endocrine tissue, by use of conventional implantation techniques. The neuronal tissue may be specific nuclei or subnuclei but can also be neural pathways between different areas of grey substance. In the treatment of e.g. Parkinson's disease, the electrodes may be implanted into the subthalamic nucleus. When the electrodes are used for treating a pain condition, they may be implanted into the periaqueductal grey substance or thalamus.

The three dimensional location of the selected group of electrodes to be used for the stimulation of the neuronal tissue is of great importance with a view to achieving an optimal or satisfactory stimulation pattern and thereby a satisfactory treatment of a specific disease condition coupled to said neuronal tissue.

It is known that there are individual differences regarding exactly which part of an excitable tissue gives the desired effect when stimulated by implanted electrodes. Thus, there is a need to optimize which electrodes are used for stimulation in each individual patient. However, promising starting points may be found by testing in animals.

The method according to the present invention may be used to determine which of several implanted individual electrodes in a bundle or array give a satisfactory effect when used to stimulate the neuronal tissue into which they have been implanted. An implanted array or bundle of multielectrodes may comprise from 10 and up to several hundreds or thousands or more even more single individual electrodes which can be used to stimulate the excitable tissue. Most often a multichannel electrode comprises 16 to 64 electrodes. In certain cases, a multichannel electrode may comprise up to 128 electrodes, such as 16 to 64, e.g. 32. This depends at least partly of the size of the target tissue.

It is important to understand that one specific individual electrode may give rise to a positive effect when stimulated alone. A specific electrode may also give rise to a negative effect or to no effect at all when stimulated alone. A specific electrode may also give rise to a positive effect only when stimulated together with one or more individual electrodes. A specific electrode may also give rise to an enhanced positive effect when stimulated together with one or more individual electrodes.

With a view to determining the optimal combination of electrodes to stimulate, a first group or cluster of a certain number of electrodes is chosen from the implanted set of electrodes for a first stimulation test. When the chosen electrodes are activated, i.e. electrically stimulates the neuronal tissue that surrounds the chosen electrodes, the patient tested or treated experiences a certain change in the symptoms of his or her underlying disease condition if one or more of the stimulated electrodes in said first group is correctly located in the neuronal tissue. Otherwise, no change or an adverse effect is experienced. Such adverse effect may be involuntary movements or mood changes. A long term adverse effect may the damage of neuronal tissue, without any positive effect regarding the condition to be treated.

Alternatively, a physiological, psychological or pathological reaction of the patient may be measured.

Feedback of the patient's experienced or perceptual change in symptoms is then mediated directly from the patient to the computer program, the computer database, and/or to the operator. This feedback or information may be given or delivered in several different ways, depending on e.g. the patient's health condition and ability to communicate the feedback. Inter alia, the patient may deliver this information by purely physical actions, such as talking, blinking, waving, movement of a certain body part etc., or by use of technical equipment (pressing a button, via a computer pad, touch screen, joystick, a touch screen, a pad a computer mouse, a trackball etc. Alternatively, the feedback may be delivered via measurement of physiological, psychological, or pathological parameters, such as blood pressure, pulse, and brain activity by use of instruments attached to the patient's body. Combinations of one or more of the above-listed ways of obtaining the feedback from the patient may also be used.

Optionally, a training period may precede the optimization of the stimulation pattern of the set of implanted electrodes.

In the case where the patient is an animal one important difference is that cognitive or perceptual changes have to be inferred indirectly, since animals cannot express the changes verbally.

It is of importance that the feedback coupled to the change of symptoms experienced is delivered by the patient itself, i.e. not the physician, doctor, nurse, medical practitioner or anyone else, who otherwise is supposed to deliver information regarding change of symptoms in conventional methods in this area. The main reason for this is that the reliability/validity of the optimization method may be substantially increased when the feedback origins directly from the patient who is subjected to the stimulation test. Other advantages with acquiring such feedback or input directly from the patient are that in the case of treatment of symptoms, especially treatment of pain, it is more effective if the information is derived from the patient directly. In addition, it is more time efficient and an effective stimulation pattern that is "good enough" may be found in less time.

In one embodiment of the present invention, when the patient provides such information, i.e. when signaling the change in symptoms, the experienced change of symptoms in question is graduated, e.g. with a view to mediating if the change is minor or major. The way of graduation of the feedback signal depends on the patient's health condition and ability to communicate as well as on the condition or disorder which is treated. A graduated scale may be used, e.g. with a score interval of 1-10. In another embodiment a continuous scale may be used, such as the VAS (visual analog scale) pain scale. For example, the VAS may be used to identify the effect of stimulation in patients suffering from pain. The scale may comprise a positive and a negative scale in order for the patient to indicate positive as well as negative effects. The feedback signal may also be binary. Any other kind of graduation means and scale intervals may be used, such as a electronic scale on a computer screen or screen of a laptop or a smartphone. Thus, all of the electrodes in said first group of electrodes are assigned a certain value, i.e. are weighted, in relation to the feedback given by the patient.

After the first stimulation step a second stimulation step is performed, wherein a second group of a certain number of electrodes is chosen from said set of implanted electrodes, and this second group of electrodes is subjected to a similar stimulation test as those in the first group, and all of the electrodes therein are assigned a certain value in a corresponding way. The number of electrodes in the second group may be different from the number of electrodes in the first group, and may also comprise one or more of the electrodes tested in the first group.

Thereafter, a third stimulation step is performed, wherein a third group of a certain number of electrodes may be chosen from said set of implanted electrodes, and the above-disclosed method steps are repeated.

The stimulation step may be performed a large number of times. Typically 10-50 groups of electrodes, preferably 15-40 groups of electrodes, are stimulated.

In one particularly preferred embodiment 20-35 groups of electrodes are subjected to the stimulation step. Each group of electrodes may contain 1-15, preferably 5-15, and most preferably 3-7, electrodes.

Typically, 20% of the total number implanted electrodes are used in each group which is used for stimulation. Every single electrode is tested at least 3 times, preferably 5 times, more preferably at least 10-15 times.

The electrodes in the total set of electrodes may belong to more than one of the groups of electrodes stimulated and are specifically indexed for that purpose. This means that different values for a specific electrode may be obtained during the different stimulation steps. Thus, combinations of electrodes which give rise to an optimal effect for the patient may be found. All of the values of the electrodes in the groups of electrodes that have been subjected to the stimulation step are recorded by a recording device R and are stored in a computer (data) program P2/P1 or a database (DB). The computer keeps track of the effects of all electrodes used.

If one specific electrode is associated with a negative effect in all or in a majority of the tests, such as a low degree of effect on the condition or disease which is treated, or such as a side effect, the groups may be tested again without this specific electrode.

When a group is tested, the stimulation parameters are set at low levels and may then gradually be increased. Especially, the values of the stimulation parameters may gradually be increased in order to accustom the patient to the stimulation. This is advantageous, since the patient is then gradually accustomed to the stimulation. In addition, a level at which the stimulation gives rise to the desired effect, but at which the stimulation does not give rise to any side effects, may be identified. If the method is preceded by an additional step of stimulating all electrodes at once while increasing the stimulation strength, the above mentioned procedure may be excluded, since the patient is already accustomed to the procedure.

The frequency used for stimulation is preferably between 130 and 160 Hz. However, for certain applications, the frequency may be lower than 130 Hz, such as 100 Hz or even lower. For other application, the frequency may be as high as 20 kHz. In one embodiment, a fixed frequency value is chosen for the stimulation test.

The amplitude used for stimulation is between 0.1 and 10 V, preferably below 2 V. For a single electrode, the desired effect is achieved up to a certain amplitude, whereafter an increase in the amplitude may give rise to side effects such as injury of the tissue. During stimulation tests, the amplitude may be varied while the frequency is kept constant.

Preferably, the shape of the pulse wave is charge balanced, such that the current of negative ions to the electrode equals the current of positive ions to the electrode. If the pulse wave is not balanced, a polarity is accumulated at the electrode interface with the tissue, which may lead to ineffective stimulation. Alternatively, but less preferred, the polarity of the stimulating electrode may be negative during the stimulation pulse, such that the stimulation originates from a cathode. In such a case, an electrical voltage is achieved at the electrode interface with the tissue, which is allowed to decay before another stimulation pulse is emitted. It is of importance that a stimulation takes place between a reference electrode and implanted electrodes or between the implanted electrodes, as the circuit has to be closed.

When all of the stimulation steps have been performed, the total assigned value for each electrode is determined by first adding the separate values assigned during the stimulation steps and then calculating the average value or median value which is used for the subsequent comparison between the potentially useful electrodes. In one embodiment the mean values and/or median values are updated during the tests performed, i.e. not only after the tests have been finalized. This calculation may be automatically performed by use of the above-mentioned computer P1/P2. Thereafter, electrodes having a total assigned value exceeding a predetermined limit value, i.e. providing an acceptable therapeutic effect, as defined above, are generally chosen for the subsequent treatment step. Correspondingly, the electrodes having the lowest total assigned value are generally deemed to not be useful. In some cases the electrodes having the highest total assigned values may be further separated into different groups and further stimulation tests may be performed with a view to finding the "best of the best" electrodes for the intended purpose. In some cases the electrodes having the highest total assigned values or all the electrodes that have a total assigned values that is above a predetermined limit may be further separated into different groups and further stimulation tests may be performed with a view to finding a group of electrodes that, when used for stimulation, give rise to the desired effect with the lowest energy consumption. This is especially advantageous, since this will prolong not only the lifespan of the battery, but may also prolong the life time of the electrodes themselves depending on the materials of the electrodes. In addition, the risk of damaging the tissue surrounding the electrodes is reduced. Furthermore, the risk of also giving rise to negative side effects is also reduced.

As stated above, generally the electrodes having the highest score are selected, but in some situations electrodes with a medium or even low score may be selected if they add positively to the therapeutic effect. This is the case when the therapeutic effect is not good enough with a smaller amount of electrodes. However, the expression "good enough" is subjective, and therefore the physician should decide whether there are reasons to increase the amount of electrodes with electrodes giving moderate or weakly positive contributions.

The total number of electrodes used for the stimulation, the total number of groups of electrodes, as well as the total number of electrodes in each group, is dependent on the underlying disease condition in question, the implantation area in the soft tissue, and the type and size of the microelectrode.

Any kind of electrode may be used. It is preferred to use microelectrodes that are spread out in and around the target tissue.

Any kind of electrode used for DBS may be used, preferably microelectrodes, that are physically separated and spread out in and around the target tissue.

Importantly, the electrodes used may be separate stimulation points, which is not the same as several electrodes located on the same construct. The difference is that tissue surrounds each electrode if they are physically separated in the tissue which allows tissue between the electrodes to be stimulated. This is not the case when electrodes are grouped together on the same physical entity. Electrodes currently used for DBS have many separate electrodes (contact points/active sites) on one physical entity. Such contact points will have contact with the tissue only on the side exposed to the tissue. Contact points/active sites located on physically separated entities such as microelectrodes that have been spread in the tissue will be surrounded by tissue and such electrodes may thus be used to stimulate tissue which is between two or more contact points/active sites.

In certain cases, larger or conventional DBS electrodes may be used.

When the electrodes having the most interesting effects, normally the highest total assigned values, average values or median values, have been determined, the spatial localization of these is thereby also known to the extent that it may be concluded that these electrodes are located in the desired brain tissue. It may be the case that the best effect is obtained from stimulation outside the nuclei, e.g. by stimulation of axons in the white substance. Thereby, no imaging step, like in conventional methods with a view to localizing the effective electrodes in the neuronal tissue, is required, which is an advantage. However, in order to update the database which is used to predict the best positions in subsequent patients, it is an advantage to determine the location of the electrodes using imaging techniques, such as e.g. CT and MRI. The continuous updating of such a database from more and more patients will likely facilitate the above described selection of the most effective electrodes and also to provide guidance to the neurosurgeon as to the optimal locations in the tissue to implant electrodes and to more exactly and accurately focus on the nuclei and/or subcompartments within nuclei and/or the precise nerve cells in question coupled to the underlying disease condition to treat or from which optimal therapeutic effects can be predicted.

The electrodes chosen in the method according to the present invention may be chosen by a computer P1, randomly or semi-randomly, or by the operator. The operator can be the patient, the animal or a responsible person, e.g. a care provider, conveying the instructions from the patient.

With a view to further facilitating the choice of effective electrodes which have been implanted in e.g. a human neuronal tissue for the stimulation of a specific nerve cell or nucleus, a predetermination step may be performed before the initiation of the optimization method according to the present invention. Said predetermination step may be based on data obtained during several tests of implanted electrodes in up to thousands or more patients in view of the specific activity pattern, sometimes also called firing pattern, each cell type produces. This data may be stored in a database DB. By referring to this database, the electrodes which are most likely to give rise to a good effect when used for stimulation of excitable tissue may be predicted. This will make the method less time consuming. Thus, this determination step may also be regarded to include the step of "listening" to the specific cell type. An implanted electrode may be used for stimulation of the neuronal tissue located in its proximity. However, the same electrode, or another electrode fixated to said electrode, may also be used to record from the neuronal tissue located in its proximity. An advantage of using one electrode for stimulation and another electrode for recording is that the properties relating to both of these activities may be optimized. For example, electrodes suitable for ejecting currents often need to have a relatively large uninsulated surface area to cause effective stimulation of nearby neurons, whereas electrodes used for recordings from single neurons should have a relatively small uninsulated surface area. When the electrode is small enough, such a recording may be considered to originate from one single cell or a few single cells. More precisely, when an electrode is implanted in such a way that it reaches a specific nerve cell, the electrical signals from the cell can be represented in a specific two-dimensional diagram, also called an activity pattern, in an extracorporeal recording device R. The two dimensions of the diagram include time on one axis and occurrence of nerve cell impulses on the other axis. Further, a specific sound may also be heard by the operator. The form of the diagram acts as a kind of fingerprint for the cell type in question. Collecting data for all kinds of cell types gives a complete bank of activity patterns, and measurements from a large number of persons give a reliable average activity pattern coupled to efficacy data, i.e. to the effect of stimulating such a cell. Thus, after collecting such data from several patients suffering from a certain condition and which are treated by electrical stimulation, predictive data concerning the effect of stimulating a cell or cells of a certain kind having a certain activity pattern is known.

In one embodiment of the present invention, such electrodes which according to the collected data stimulate cells that are likely to give rise to a positive effect when stimulated, are chosen to be included in the groups which are used for finding the most optimal stimulation pattern. In other words, electrodes chosen in this way are likely to give rise to a positive effect when used for stimulation of the excitable tissue. The chosen electrodes are then used for stimulation and the information obtained from the patient is recorded as described above. Thus, according to one embodiment, the present invention also comprises the steps of recording the activity pattern of each implanted electrode of a patient, optionally identifying the type of cell or cells from which the electrode is recording the activity pattern, and choosing the electrode groups based on the recorded activity patterns.

For choosing the electrodes which are to be used in the stimulation, two sets of electrodes may be used. The first set comprises electrodes which are used for recording signals from the neuronal tissue and the second set of electrodes comprises electrodes which may be used for stimulation. Each electrode belonging to the second set of electrodes may have an electrode from the first set fixated to it. In this way, the signals recorded from the first electrode may be used to determine the (approximate) location of the electrode to which it is fixated, i.e. to determine the electrodes which can be used for stimulation. Alternatively, the electrodes belonging to the first set are not fixated to electrodes belonging to the second set, but arranged in such a way that, when implanted, an electrode from the first set is implanted in close proximity to an electrode belonging to the second set. In this way, different electrode pairs can be identified and suitable electrodes belonging to the second set may be selected by recording from a corresponding electrode belonging to the first set.

Preferably, the electrodes used for registration are not used for stimulation. The electrodes used for registration provide information regarding the anatomical locations in the target area that is to be stimulated. Thus, according to one embodiment of the invention, stimulation is made through electrodes nearby the recording electrodes that show the most promising activity pattern(s).

In addition, the above mentioned method of recording the firing pattern from cells located in the proximity of the implanted electrodes may be used to exclude from the groups to be tested electrodes which have been identified as recording from/stimulating cells which give rise to negative effects. This further optimizes the method according to the present invention.

When the three dimensional electrode location giving the optimal stimulation pattern for the treatment of a certain disease condition coupled to certain tissue has been determined, the treatment and energy consumption may be further improved by adjusting such parameters as the pulse width, the amplitude, the stimulation strength, the temporal pattern of stimulation, the shape of the individual stimulation pulse, the polarity, the stimulation type (randomized or semi-randomized, sequential), and the frequency and/or by use of a modulated currency field, e.g. by letting the amplitude of the stimulation pulse vary over time. The stimulation may also be frequency modulated over time or applied as short lasting high frequency bursts interspersed with lower stimulation frequencies.

In one embodiment the method according to the present invention also includes the additional step of optimizing the energy consumption while achieving an acceptable therapeutic effect. The values of the stimulation parameters, preferably one or more of the following parameters: the amplitude, the wave shape of the electrical pulse (such as e.g. sinus-formed and square-formed), the pulse length, and the frequency used during the stimulation, may be optimized. This can be accomplished by the stimulation of the chosen electrode set repeated times at different values of these parameters. E.g., in a first test series the stimulation strength and the wave shape may be held constant while the frequency is varied at different values. In a second test series the stimulation strength and the frequency may be held constant while the wave shape is varied in different ways, and in a third test series the wave shape and the frequency are held constant while the stimulation strength (either voltage or current intensity) is varied at different values. In a further version, two of these three parameters are varied during the test while one of them is held constant. The amount of different values tested during each test is not restricted, but normally up to 5 different values of each parameter are tested. In another version each one of said parameters may be varied according to a sliding scale. The therapeutic effect is monitored (e.g. through feedback from the patient as previously described) and the energy consumption is recorded. The energy consumption may be transformed into a scale similar to the scale for registering the therapeutic effect.

Other examples of parameters which may optimized comprise the pulse width, the stimulation strength, the shape of the stimulation pulse, the polarity, the stimulation type as to the degree of randomization and the temporal pattern of stimulation, e.g. periods of higher frequency followed by lower frequencies or quisence as when burst stimulation is used, wherein the internal frequency of pulses in the burst is higher than the frequency of the bursts. One example is to use bursts with 3-10 pulses, internal frequency exceeding 200 Hz wherein the bursts are separated by a period of less frequent stimulation. Another pattern is to use amplitude modulation or frequency modulation. In the first case amplitude modulation means that the pulse amplitude (either voltage or current intensity) is varied over a certain time cycle between defined values. Frequency modulation means that the frequency is varied in same way. The modulation may be e.g. sinusoidal variation of pulse amplitude or frequency.

The energy consumption of each pulse can be calculated by a person skilled in the art given that the current and voltage is measured. Given that the voltage and current do not change significantly during the time interval measured, the energy consumption in each pulse may be calculated as absolute voltage×absolute current×time interval of the pulse. A measurement of the current and voltage of each pulse and the total number of pulses is in this case therefore enough for calculation a value for the energy consumption during each test series. In cases where the voltage and current changes during the pulse such as for e.g. a sinusoidal pulse, the energy consumption in each pulse may be calculated as the integral of the absolute (voltage×current) over time, i.e.

$$\int_{t_1}^{t_2} u(t)i(t)dt$$

where u(t) is the voltage at time t and i(t) is the current at time t, and
where $t_1$ denotes time of onset of the pulse and $t_2$ denotes the end of the pulse.

The energy consumption may be calculated as the energy consumption in each pulse multiplied with the total number of pulses in the test. The total energy consumption of the treatment will also include energy consumption in the electronics and battery used to stimulate the tissue.

The tested group of electrodes is assigned a value based on the therapeutic effect and on the energy consumption.

The assigned value may be a function of the therapeutic effect and the energy consumption.

The therapeutic effect and the energy consumption may be given different weight when assigning the value. The assigned value can be written as $$k(\text{therapeutic effect}) + \frac{m}{\text{energy consumption}}$$

wherein k and m are predetermined constants.

In order to assign a value to a tested group, the therapeutic effect may have to be above a certain predetermined threshold and/or the energy consumption may have to be below a certain predetermined threshold. Thus, if a certain set of stimulation parameters does not give an acceptable therapeutic effect, then m/(energy consumption)=0.

When the parameter tests have been performed and a value has been assigned for each set of parameter values, the parameter set with the highest value, total value, average value or median value, is chosen for the subsequent stimulation treatment of the patient with the chosen set of electrodes.

Reducing the energy consumption is desired, since this will lead to a longer lifespan of the battery of the stimulation device connected to the implanted electrodes. In most cases, the battery is implanted under the chest of the patient and thus a battery change always involves a surgical procedure. By extending the lifespan of the battery, the time interval between these procedures is prolonged. In case rechargeable batteries are used longer time periods in between recharging can be obtained which is more convenient for the patient. Furthermore, the present invention, by reducing the energy demand, will also allow smaller batteries, which today make up a large fraction of the electronics. This will open up for smaller electronic implants that can be placed closer to the target tissue. Long connecting cables to the electronics, which can cause discomfort to the patient, may thus be avoided. Also, the size of the electronics of the stimulator depends a lot on the size of the battery. So if the energy consumption can be reduced the battery can be reduced in size and therefore also the stimulating device.

In addition, lower currents emitted from the implanted electrodes and therefore also lower energy consumption will also lead to a reduced risk of damaging the tissue surrounding the electrodes. A lower energy consumption will also cause less heat dissipation from the electrodes and electronics which is beneficial for the tissue around the electrodes and electronics. Lower currents emitted from the implanted electrodes and therefore also lower energy consumption may lead to a reduced risk of the stimulation resulting in unwanted side effects, i.e. stimulation of neurons which do not contribute (or which have a negative effect on the therapeutic effect) to the desired effect may be avoided or reduced. Thus, the stimulation may be more targeted to neurons which when stimulated contribute to the desired effect.

The main purpose of optimizing the energy consumption is to maintain satisfactory stimulation treatment results, while at the same time the energy consumption is reduced. This purpose may be fulfilled in several different ways.

First, the optimization of the stimulation pattern of implanted electrodes disclosed throughout the application text above leads to the use of a lower amount of electrodes for obtaining the same stimulation result. Thus, reducing the group of implanted electrodes to a sub-group of electrodes which are used for stimulation still providing satisfactory results will as such significantly reduce the energy expenditure.

Second, the design of the electrodes may be adapted to the treatment of the tissue in question. Different effective electrode designs and structures are disclosed in the patent literature. However, the well-known problem of the formation of kill zones in the tissue volume surrounding the electrodes has now been observed to occur in particular when large electrodes are used (Thelin J, Jörntell H, Psouni E, Garwicz M, Schouenborg J, Danielsen N, Linsmeier C E. Implant size and fixation mode strongly influence tissue reactions in the CNS. PLoS One. 2011 Jan. 26; 6(1): e16267).

Third, as also discussed above, the treatment and the energy consumption may be further improved by adjusting parameters such as the pulse width, the amplitude, the stimulation strength, the temporal pattern of stimulation, the shape of the individual stimulation pulse, the polarity, the stimulation type (randomized or semi-randomized, sequential), and the frequency and/or by use of a modulated current field, e.g. by letting the amplitude of the stimulation pulse vary over time. The stimulation may also be frequency modulated over time or applied as short lasting high frequency bursts interspersed with lower stimulation frequencies.

Fourth, the stimulation can be arranged to be controlled by the patient only, i.e. in such a way that stimulation only is performed when really required. Thereby, no unnecessary energy consuming stimulation is performed.

In one embodiment the method according to the present invention also includes the complementary steps of optimizing certain stimulation parameters with an ultimate view to improving the result of the stimulation treatment of patients.

In a first version of this embodiment, the following applies. When the preferred electrodes have been selected according to the inventive method, the stimulation treatment may be further improved by optimizing the values of the stimulation parameters, preferably one or more of the following parameters: the amplitude, the wave shape of the electrical pulse (such as e.g. sinus-formed and square-formed), the pulse duration and the frequency used during the stimulation. This can be accomplished by the stimulation of the chosen electrode set repeated times at different values of these parameters. E.g., in a first test series the amplitude, the wave shape, and the pulse duration may be held constant while the frequency is varied at different values. In a second test series the amplitude, the pulse duration, and the frequency may be held constant while the wave shape is varied in different ways. In a third test series the wave shape, the pulse duration, and the frequency are held constant while the amplitude is varied at different values. In a fourth test the amplitude, the wave shape and the frequency may be held constant while the pulse duration is varied at different values. In a further version, two or three of these four parameters are varied during the test while the other(s) are/is held constant. The amount of different values tested during each test is not restricted, but normally up to 5 different values of each parameter are tested. In another version each one of said parameters may be varied according to a sliding scale. The values are chosen from feedback from the patient, who will signal when the effect is better or worse when the amplitude is increased or decreased, or when the frequency is increased or decreased etc. By adjustment of a sliding scale the parameter for stimulation of the intended group of electrodes may be tuned.

For each test, the patient provides information or feedback of the perception of the stimulation in the same way as described above. When the parameter tests have been performed and a value has been assigned for each set of parameter values, the parameter set with the highest value, total value, average value or median value, is chosen for the subsequent stimulation treatment of the patient with the chosen set of electrodes. In such a way, both the electrode set used for the stimulation and the stimulation parameters are improved.

In a second version of this embodiment, the following applies. The parameter value variation tests disclosed above may be performed in the method according to the present invention in connection with the stimulation test of each one of one or more of the groups of electrodes, wherein each electrode in each group is assigned a value related to the information or feedback provided by the patient. In addition, the energy consumption may be recorded and used as described above when assigning a value to the tested group of electrodes.

Thus, instead of just one stimulation test, i.e. one set of parameters, for each group of electrodes as in the inventive method, several stimulation tests with variations of the four above-mentioned parameters as disclosed above are performed for each group of electrodes. In such a way, a preferred stimulation parameter set for each group of electrodes stimulated is obtained. When all of the different groups of electrodes have been tested and the electrodes having the highest assigned values, total values, average values or median values, have been chosen, the parameter values coupled to the assigned values are checked and the best ones are chosen for each individual electrode in the subsequent stimulation treatment. Further, the parameter variation values tested may differ for the different electrode groups tested. In this case, known mathematical and statistical methods, such as e.g. multivariate analysis, are used to identify the optimal parameter values.

The embodiments involving the parameter value variation tests is more time-consuming and demanding for the patient, since these embodiments require that the patient becomes subjected to more tests compared to when the inventive method is performed at constant parameter values throughout the stimulation tests. The use of the parameter value variation tests should therefore be balanced with the curing and relief effects obtained for the patient due to this parameter optimization.

In another embodiment further of the above listed parameters, such as stimulation polarity, stimulation strength, and temporal pattern of stimulation, may be varied in the parameter value variation tests in addition to or instead of the four above-mentioned parameters.

In another embodiment of the invention, stimulation parameters are chosen so that an electrical field is created between the electrodes used for the stimulation, wherein the electrical field has a direction which allows the neurons located in the directed electrical field to be stimulated. An advantage of this embodiment is that less energy is needed in order to stimulate the targeted neurons when the electrical field is directed along the main axis of these neurons, as explained above. This may lead to a more specific stimulation, reducing the risks of side effects.

In one embodiment of the invention, the chosen parameters are also stored in the database and may thus be used to choose parameters which are more likely to result in the desired therapeutic effect. This will further contribute to shorten the time needed to optimize the stimulation.

In one specific embodiment of the invention, the patient controls the selection of the electrodes using for example an interactive screen or joystick to be moved in a search field. A search field in this context is a sub-area of a sub-group of electrodes in the X-Y plane in which sub-area the individual electrodes are represented with a unique coordinate.

In another specific embodiment of the invention, the patient controls the selection of the electrodes using for example an interactive screen or joystick to move a search field which in this context is a delineated subgroup of electrodes in the X-Y plane in which the individual electrodes are represented with a unique coordinate.

When the search field is moved by use of the joystick or the cursor, one electrode is replaced with a new one. In this case it is advantageous if the electrodes are grouped in such a way that adjacent electrodes in the target tissue also are adjacent in said X-Y plane. In one version, the patient, while moving around said search field, provides feedback to a microprocessor or computer by indicating the effectiveness of the present selection of electrodes or selection of stimulation parameters of the individual electrodes or groups of electrodes in reducing the symptoms. This feedback from the patient is stored in the computer. This feedback can be provided verbally by the patient, or for example using a cursor on a computer screen. It can also be provided by measured signals, such as blood pressure, tremor, EEG or by implanted electrodes in relevant brain centers in the patient or animal. The energy cost for each selection is also computed and stored together with patient feedback. Based on several iterations, the computer or microprocessor calculates the cost benefit ratio for each electrode in order to predict the optimal selection and stimulation parameters of electrodes.

To optimize the stimulation parameters, the amplitude, frequency etc for the group may be varied up and down using a joystick or a button which can be turned clockwise (signaling increase of the parameter) or anticlockwise (signaling decrease of the parameter) etc., the effectiveness noted and stored in the computer/database. The parameters may be further fine tuned by evaluating the effect of each electrode separately such that the parameter to be tested is changed selectively for that electrode.

In another embodiment the patient and the physician need not to be in the same location, since the device associated with the implant and the computer controlling the settings of the stimulation may communicate over the internet. E.g. a fine tuning of the stimulation parameters such as stimulation amplitude, frequency, pulse shape may be made in this way. This is especially advantageous, since the fine tuning of the stimulation may be performed when the patient is in his home. Also in this case it is advantageous if the patient first is allowed to get accustomed with the technique during the surveillance, wherein the confidence is increased and the anxiety due to the implant is reduced.

Other objectives, features and advantages of the present invention will appear from the detailed disclosure above, from the attached claims, as well as from the drawings. It is noted that the invention relates to all possible combinations of features.

Generally, all terms used in the claims are to be interpreted according to their ordinary meaning in the technical field, unless explicitly defined otherwise herein. All references to "a/an/the [electrode, device, step, etc.]" are to be interpreted openly as referring to at least one instance of said electrode, device, step, etc., unless explicitly stated otherwise. The steps of any method disclosed herein do not have to be performed in the exact order disclosed, unless explicitly stated.

As used herein, the term "comprising" and variations of that term are not intended to exclude other additives, components, integers or steps.

The invention claimed is:

1. A method for optimization of a stimulation specificity and an energy consumption of implanted electrodes in excitable tissue of a patient, the method comprising:

electrically stimulating excitable tissue between each of one or more different combinations of electrode pairs in a cluster of electrodes, or electrically stimulating excitable tissue between each of one or more different combinations of electrode pairs in two or up to 50 clusters of electrodes, each cluster containing 1-15 electrodes, wherein two electrodes of the electrode pairs do not belong to a same cluster;

wherein each of the electrodes is located on a physically separated entity, such that the tissue surrounds and separates each electrode from all other electrodes, thereby allowing tissue between the electrodes to be stimulated;

wherein the electrodes are microelectrodes having a diameter of less than 100 μm;

choosing an electrode pair or pairs which give rise to a lowest energy consumption while still giving a therapeutic effect, or assigning each electrode pair a value related to the information provided by the patient and the energy consumption, and choosing the electrode pair or pairs which give(s) rise to a most favorable assigned value; and then stimulating the chosen electrodes to treat or alleviate a neurological disease or condition of the patient.

2. The method according to claim 1, wherein positions of the individual implanted electrodes spread out in the tissue are determined using imaging techniques; and wherein electrode pairs containing electrodes a location of which is previously known to give a therapeutic effect or to not give rise to adverse effects are stimulated.

3. The method according to claim 1, wherein the electrical stimulation between different combinations of electrode pairs in the cluster of electrodes, or the electrical stimulation between different combinations of electrode pairs in the two or more clusters of electrodes, creates a directed electrical field;

wherein an effect of the directed electrical field is assessed after each electrical stimulation by registering information provided from the patient in view of a therapeutic effect and by monitoring an energy consumption; and wherein the electrodes of the electrode pairs are positioned in two different electrode clusters located close to neurons occupying two separate hemispheres of tissue or in such a way that an electrical field obtained is directed along a main axis of neurons.

4. The method according to claim 1, wherein the electrical stimulation between different combinations of electrode pairs in the cluster of electrodes, or the electrical stimulation between different combinations of electrode pairs in the two or more clusters of electrodes, creates a directed electrical field;

wherein an effect of the directed electrical field is assessed after each electrical stimulation by registering information provided from the patient in view of a therapeutic effect and by monitoring an energy consumption;

wherein the cluster of electrodes or the two or more clusters of electrodes comprises(s) electrodes chosen to be included in a stimulation pattern obtained by a method for optimization of the stimulation pattern of a set of implanted electrodes in excitable tissue of a patient, comprising:

(a) choosing a first group of a certain number of electrodes from the set of implanted electrodes, (b) stimulating the excitable tissue electrically by the first group of electrodes, (c) registering information provided by the patient in response to the stimulation, and (d) assigning each electrode of the first group of electrodes a value related to the information, wherein steps (a)-(d) are repeated for one or more further groups of the certain number of electrodes chosen from the set of implanted electrodes, wherein each electrode may be included in one or several groups, wherein a total assigned value for each electrode is calculated, wherein electrodes having a total assigned value exceeding a predetermined value or a predetermined number of the electrodes having a highest total assigned value are chosen to be included in the stimulation pattern, and wherein steps (a)-(d) are preceded by stimulating all electrodes at the same time while increasing the stimulation strength up to a threshold such that the patient is gradually acquainted to the effect of stimulation.

5. The method according to claim 4, further comprising a second optimization of stimulation parameters for the electrodes chosen to be included in the stimulation pattern according to claim 4 in view of the energy consumption needed for the chosen electrodes to give rise to a therapeutic effect, wherein the second optimization comprises:

varying one or more of the stimulation parameters for the chosen electrodes in a stimulation test series;

registering information provided by the patient;

monitoring the energy consumption for each stimulation test where the stimulation gives rise to a therapeutic effect; and choosing, as the stimulation parameters, the parameters which give rise to the lowest energy consumption while still giving a therapeutic effect; or assigning each stimulation test a value related to the information provided by the patient and the energy consumption; and choosing the parameters which give rise to the most favorable assigned value.

6. The method according to claim 5, further comprising:

optimizing one or more stimulation parameters for the use of the electrodes chosen to be included in the stimulation pattern in a stimulation treatment of the patient, wherein the chosen electrodes are subjected to stimulation tests in which one or more stimulation parameters chosen from the group comprising a pulse width, an amplitude of a stimulation pulse, a stimulation strength, a stimulation frequency, a temporal pattern of stimulation, a shape of the stimulation pulse, a polarity, a stimulation type as to a degree of randomization, amplitude modulation, and frequency modulation are varied, wherein information provided by the patient is registered for each stimulation test, wherein each parameter set is assigned a value related to the information, and wherein the parameter set having a most favorable assigned value is chosen to be used for the chosen electrodes during the stimulation treatment, or wherein the one or more stimulation parameters also are used in the stimulation test of the second optimization in view of energy consumption according to claim 5.

7. The method according to claim 6, wherein one or more of the amplitude of the stimulation pulse, the stimulation frequency, and the shape of the stimulation pulse are varied in each stimulation test.

8. The method according to claim 5, further comprising:

optimizing one or more stimulation parameters for a use of the electrodes chosen to be included in the stimulation pattern in a stimulation treatment of the patient, wherein the chosen electrodes are subjected to stimulation tests in which a burst mode is varied, wherein information provided by the patient is registered for each stimulation test, wherein each parameter set is assigned a value related to the information, and wherein the parameter set having the most favorable assigned value is chosen to be used for the chosen electrodes during the stimulation treatment, or wherein one or more stimulation parameters also are used in the stimulation test of the second optimization in view of energy consumption according to claim 5.

9. The method according to claim 4, wherein the set of implanted electrodes comprises a plurality of microelectrodes.

10. The method according to claim 4, wherein the excitable tissue is neuronal tissue or endocrine tissue, a heart or a vascular system.

11. The method according to claim 10, wherein the neuronal tissue is brain tissue, spinal cord or peripheral nerves.

12. The method according to claim 11, wherein the brain tissue is selected from the group consisting of subthalamic nucleus (STN), globus pallidus interna (GPi), periaqueductal grey substance, periventricular grey, internal capsule, ventral posterolateral nucleus, thalamus, striatum, habenula, hypothalamus, basal nucleus of Meynert, cortical areas, brain stem, medial forebrain bundle, internal capsule, amygdala, hippocampus, septum, and ventral posteromedial nucleus.

13. The method according to claim 10, wherein the endocrine tissue is selected from the group comprising pancreas, pituitary gland and pineal gland.

14. The method according to claim 4, wherein each group of electrodes is chosen randomly.

15. The method according to claim 4, wherein each group of electrodes is chosen by:

recording of an activity pattern in the excitable tissue by each implanted electrode, identifying an anatomical compartment or type of cells from which the electrode is recording the activity pattern, comparing the recorded activity pattern with information stored in a database, and choosing the group of electrodes to be used for stimulation on a basis of a result of the comparing and/or on a basis of the identified anatomical compartment.

16. The method according to claim 4, wherein each group of electrodes is chosen by:

recording of activity pattern in the excitable tissue by each implanted electrode, identifying an anatomical compartment or type of cells from which the electrode is recording the activity pattern, and choosing the group of electrodes to be used for stimulation on a basis of the recorded activity patterns and/or on a basis of the identified anatomical compartment.

17. The method according to claim 16, further comprising:

coupling the anatomical compartment or type of cells with the information from the patient in a database, and coupling combinations of electrodes which stimulate certain anatomical compartments or types of cells to the information from the patient in a database.

18. The method according to claim 4, wherein each group of electrodes is chosen by:
performing brain scanning, MRI examination, CT examination and/or ultrasound examination,
identifying anatomical compartments where the electrodes are located, and
choosing the group of electrodes on a basis of a location of the electrodes.

19. The method according to claim 4, wherein a number of electrodes in each group is 1-15, or wherein at most 50% of a total number of electrodes are included in each group.

20. The method according to claim 4, wherein the information from the patient is a response to an effect of the stimulation perceived by the patient.

21. The method according to claim 4, wherein the information from the patient is a value obtained by measuring a physiological, psychological or pathological reaction of the patient.

22. The method according to claim 4, wherein the information from the patient is a combination of a response to an effect of the stimulation perceived by the patient and a value obtained by measuring a physiological, psychological or pathological reaction of the patient.

23. The method according to claim 4, wherein the information from the patient is binary.

24. The method according to claim 4, wherein the information from the patient is given on a scale.

25. The method according to claim 4, wherein 10-50 different groups of electrodes are stimulated.

26. The method according to claim 4, wherein the information from the patient is provided by use of a joystick, a touch screen, a pad, a computer mouse and/or a trackball.

27. The method according to claim 4, wherein the information from the patient is provided via a device registering eye movements.

28. The method according to claim 4, wherein the method steps are preceded by a step in which the patient is allowed to get accustomed to a plurality of conditions and equipment utilized during the stimulation.

29. The method according to claim 4, wherein the stimulation and the provision of information is performed by the patient via an electronic connection with a practitioner/physician.

30. The method according to claim 4, wherein the method is followed on a screen device on which the implanted electrodes in the tissue are graphically represented, and
wherein the patient has an ability to scan the groups of electrodes to stimulate the tissue.

31. A method for treatment or alleviation of a disease or condition by use of a set of electrodes whose stimulation pattern has been optimized with the method according to claim 4,
wherein the disease or condition is chosen from the group consisting of brain and/or spinal damage, lost functions, pain, Parkinson's disease, tremor, motor disorders, choreatic and other involuntary movements, memory disorders, Alzheimer's disease, degenerative diseases, epilepsy, mood disorders, aggression, anxiety, phobia, affect, sexual over-activity, impotence, eating disorders, sleep disorders, such as narcolepsy, attention disorders, stroke, damage of the brain, damage of the spinal cord, bladder disorders after spinal cord injury, bowel disorders after spinal cord injury, spasticity, somatosensory disorders, auditory disorders, visual disorders, and olfactory disorders.

32. A system for optimization of the stimulation pattern of a set of electrodes adapted to be implanted in excitable tissue of a patient and for treatment or alleviation of disease or disorder with the method according to claim 4, the system comprising:
a set of electrodes adapted to be implanted in excitable tissue of a patient, wherein each of the electrodes is located on a physically separated entity, thereby allowing tissue to surround and separate each electrode from all other electrodes and allowing tissue between the electrodes to be stimulated,
a stimulation device connected to the set of electrodes and adapted to stimulate the excitable tissue via the set of electrodes, wherein the stimulation device is adapted to activate the set of electrodes at the same time while increasing a stimulation strength,
a first computer program connected to the stimulation device and configured to transform information provided by the patient to an assigned value for a tested group of electrodes, to calculate a total assigned value for each electrode, and to choose a preferred set of electrodes to be used for stimulation treatment,
wherein the first computer program is configured to choose a group of electrodes from the set of implanted electrodes and to instruct the stimulation device to stimulate the tissue through these electrodes.

33. The system according to claim 32, further comprising:
a recording device connected to the set of electrodes and adapted to register an activity pattern in the excitable tissue,
a second computer program connected to the recording device and to the first computer program, and
a database connected to the first computer program and to the second computer program,
wherein the second computer program is configured to compare information obtained from the recording device in view of the registered activity pattern in the excitable tissue with information in the database in the form of previously registered activity patterns for several patients regarding the effect of stimulation of the same or similar excitable tissue of the several patients, to choose a collection of useful electrodes with the basis on the comparison of activity patterns, and to transform the information about the chosen electrodes to the first computer program,
wherein said first computer program is configured to transmit the information provided by the patient to the database for storage.

34. The system according to claim 32, wherein the set of implanted electrodes comprises a plurality of microelectrodes.

35. The system according to claim 32, further comprising a joystick, a touch screen, a tablet, a computer mouse and/or a trackball,
wherein the joystick, touch screen, pad, computer mouse and/or trackball is used by the patient to provide the first computer program with information.

36. The system according to claim 32, further comprising a device registering eye movements,
wherein the device registering eye movements is used by the patient to provide the first computer program with information.

37. The system according to claim 32, further comprising a screen device on which the implanted electrodes in the tissue are graphically represented.

* * * * *